United States Patent
Cardosa et al.

(10) Patent No.: US 10,555,997 B2
(45) Date of Patent: *Feb. 11, 2020

(54) ANTIGENS AND VACCINES DIRECTED AGAINST HUMAN ENTEROVIRUSES

(71) Applicant: SENTINEXT THERAPEUTICS Sdn Bhd, Penang (MY)

(72) Inventors: Mary Jane Cardosa, Kuala Lumpur (MY); Mohamad Fakruddin Jamiluddin, Frederick, MD (US); Sharifah Binti Hamid, Shah Alam (MY)

(73) Assignee: SENTINEXT THERAPEUTICS Sdn Bhd, Penang (MY)

( * ) Notice: Subject to any disclaimer, the term of this patent is extended or adjusted under 35 U.S.C. 154(b) by 0 days.

This patent is subject to a terminal disclaimer.

(21) Appl. No.: 15/964,198

(22) Filed: Apr. 27, 2018

(65) Prior Publication Data

US 2018/0271971 A1 Sep. 27, 2018

Related U.S. Application Data

(62) Division of application No. 14/402,495, filed as application No. PCT/IB2012/003114 on Nov. 1, 2012, now Pat. No. 9,987,350.

(30) Foreign Application Priority Data

Nov. 3, 2011 (MY) .............................. PI2011005318

(51) Int. Cl.
  *C12N 15/00* (2006.01)
  *A61K 39/125* (2006.01)
  (Continued)

(52) U.S. Cl.
  CPC ............ *A61K 39/125* (2013.01); *A61K 39/12* (2013.01); *A61K 39/13* (2013.01); *C12N 7/00* (2013.01);
  (Continued)

(58) Field of Classification Search
  None
  See application file for complete search history.

(56) References Cited

U.S. PATENT DOCUMENTS

| 4,508,708 A | 4/1985 | Van Wezel |
| 2003/0158141 A1* | 8/2003 | Gromeier ............... C12N 15/86 514/44 R |

(Continued)

FOREIGN PATENT DOCUMENTS

| CN | 101831410 | 9/2010 |
| WO | WO2011048353 | 4/2011 |

OTHER PUBLICATIONS

Yozwiak et al., "Human Enterovirus 109: a Novel Interspecies Recombinant Enterovirus Isolated from a Case of Acute Pediatric Respiratory Illness in Nicaragua," Journal of Virology, vol. 84, No. 18 (Year:2010).*

(Continued)

*Primary Examiner* — M Franco G Salvoza
(74) *Attorney, Agent, or Firm* — Hueschen and Sage

(57) ABSTRACT

The instant invention provides materials and methods for producing immunologically active antigens derived from members of the Picornaviridae virus family. The picornavirus antigens of the invention may be in a form for use as a vaccine administered to a subject in a therapeutic treatment or for the prevention of a picornavirus infection. The picornavirus antigens of the invention may be in the form of an immunogenic composition for use in vaccines which are administered for the prevention of an *Enterovirus* infection.

(Continued)

The instant invention further encompasses immunogenic compositions comprising Human *enterovirus* A, Human *enterovirus* B, Human *enterovirus* C, Human *enterovirus* D antigens and their use in vaccines for the prevention of an *Enterovirus* infection.

3 Claims, 25 Drawing Sheets

Specification includes a Sequence Listing.

(51) Int. Cl.
*A61K 39/12* (2006.01)
*A61K 39/13* (2006.01)
*C12N 7/00* (2006.01)
*A61K 39/00* (2006.01)

(52) U.S. Cl.
CPC ................ *A61K 2039/5256* (2013.01); *A61K 2039/5258* (2013.01); *A61K 2039/70* (2013.01); *C12N 2710/14043* (2013.01); *C12N 2770/32323* (2013.01); *C12N 2770/32334* (2013.01); *C12N 2770/32351* (2013.01); *C12N 2770/32371* (2013.01); *C12N 2770/32634* (2013.01); *Y02A 50/466* (2018.01)

(56) References Cited

U.S. PATENT DOCUMENTS

| | | | | |
|---|---|---|---|---|
| 2005/0112095 | A1* | 5/2005 | Hsu ...................... | C07K 14/005 424/93.2 |
| 2006/0182762 | A1 | 8/2006 | Irene Martina Maas et al. | |
| 2007/0015243 | A1 | 1/2007 | Aguirre | |
| 2009/0304729 | A1 | 12/2009 | Gregersen | |
| 2010/0143406 | A1 | 6/2010 | Smith | |
| 2010/0183649 | A1 | 7/2010 | Wang et al. | |
| 2014/0127216 | A1 | 5/2014 | Balraj | |

OTHER PUBLICATIONS

Chung, Cheng-Yu, et al., "Enterovirus 71 virus-like particle vaccine: Improved production conditions for enhanced yield", Vaccine, vol. 28, No. 43,Oct. 2010,pp. 6951-6957.
Chung, Yao-Chi, et al., "Immunization with virus-like particles of enterovirus 71 elicits potent immune repsponses and protects mice against lethal, challenge", Vaccine, vol. 26, No. 15, Mar. 2008, pp. 1855-1862.
International Search Report and Written Opinion for PCT/IB2012/003114 dated Sep. 13, 2013.
Matrahim, N., et al., "DNA Vacine Construct in the Presence of EV71 IRES Elicited Higher Neutralizing Antibody Titre", International Journal of Infectious Diseases, vol. 12, No. Suppl. 1, Dec. 2008, p. E254.
Ansardi, David, C., et al., "Coinfection with recombinant vaccinia viruses expressing poliovirus P1 and P3 proteins results in polyprotein processing and formation of empty capsid structures", Journal of Virology, Apr. 1991, pp. 2088-2092.
Basavappa, R., et al., "Role and mechanism of the maturation cleavage of VP0 in poliovirus assembly: Structure of the empty capsid assembly intermediate at 2.9 Å resolution", Protein Science, 1994, 3:1651-1669.
Chung et al., "Expression, purification and characterization of enterovirus-71 virus-like particles", World J Gastroenterol, 12(6): 921-927, 2006.
Chung, et al., "Enterovirus 71 virus-like particle vaccine: Improved production conditions for enhanced yield", Vaccine, vol. 28, Issue 43: 6951-6957, 2010.
Chung, Yao-Chi, "The expression and characterization of enterovirus 71 virus-like particles and following evaluation as a potential vaccine", Jul. 2008, Dissertation, Department of Chemical Engineering, National Tsing Hua University, Taiwan.
Chung, Yao-Chi, "The expression and characterization of enterovirus 71 virus-like particles and following evaluation as a potential vaccine", Jul. 2008, Dissertation, Department of Chemical Engineering, National Tsing Hua University, Taiwan; Abstract Translation.
CN101831410,University Beijing Technology, published Sep. 15, 2010_English language translation.
Hober et al., "Enteroviral Pathogenesis of Type 1 Diabetes", Discov Med 10(51): 151-60, 2010.
Hu et al., "Formation of enterovirus-like particle aggregates by recombinant baculoviruses co-expressing P1 and 3CD in insect cells", Biotechnology Letters, 25: 919-925, 2003.
Junemann, Christiane, et al. "Picornavirus internal ribosome entry site elements can stimulate translation of upstream genes"; Journal of Biological Chemistry, vol. 282, No. 1, Jan. 5, 2007, pp. 132-141.
Lin, Yu-Li, et al. Vaccine 30:1305-1312, 2012.
Liu et al., "Direct Interaction between Two Viral Proteins, the Nonstructural Protein 2CATPase and the Capsid Protein VP3, Is Required for Enterovirus Morphogenesis", PLoS Pathogens, vol. 6, Issue 8: e10010066, 2010.
Liu, Q., et al., "Detection, characterization and quantitation of coxsackievirus A16 using polyclonal antibodies against recombinant capsid subunit proteing", J. Virol Methods, Apr. 2011; 173(1), pp. 115-120.
Oh et al., "Insight into Poliovirus Genome Replication and Encapsidation Obtained from Studies of 3B-3C Cleavage Site Mutants", Journal of Virology, vol. 83, No. 18, 2009.
Pathinayake et al., "Innate Immunity and Immune Evasion by Enterovirus 71", Viruses, 7(12): 6613-30, 2015.
Urakawa, et al. J. gen. Virol. 70:1453-1463, 1989.
Vogt et al., "An RNA Element at the 5'-End of the Poliovirus Genome Functions as a General Promoter for RNA Syntheses", PLoS Pathogens, vol. 6, Issue 6: e1000936, 2010.
Xu, Juan, et al., "EV71: An emerging infectious disease vaccine target in the Far East?", Vaccine, 28, 2010, pp. 3516-3521.
Yee et al., "Development of Novel Vaccines against Enterovirus-71", Viruses, 8(1): 1, 2016.
Chung, Yao-Chi, et al. Expression, purification and characterization of enterovirus-71 virus-like particles. World J Gastroenterol. 12:921.-927, 2006.
Liu, et al. "A virus-like particle vaccine for coxsackievirus A16 potently elicits neutralizing antibodies that protect mice against lethal challenge", Vaccine, 30(47):6642-6648, Sep. 7, 2012.
Tee, et al. Journal of Virology, 84:3339-3350, 2010.

* cited by examiner

Figure 1. HEV71 VLP expression cassette [P1+IRES+3CD] and the pSN01 plasmid.

Figure 2. HEV71 VLP expression cassette [P1+IRES+3C] and the pSN03 plasmid.

Figure 3. Expression of VP1 in supernatant of SN07 infected Sf9 cells.

Figure 4. Processed VP1 in both the supernatants and the lysates.
    Lanes 1 and 5: bacSN07p3
    Lanes 2 and 6: bacSN08p3
    Lanes 3 and 7: bacGUSd2
    Lanes 4 and 8: Sf9 control Figure 5. VP1 and VP0 are in the retentate after ultrafiltration over a 100kDa molecular weight cut off (MWCO) membrane.

Figure 7. Immunoblots probed with rabbit polyclonal antisera against VP0 (arrow) at 3 different times of harvest.
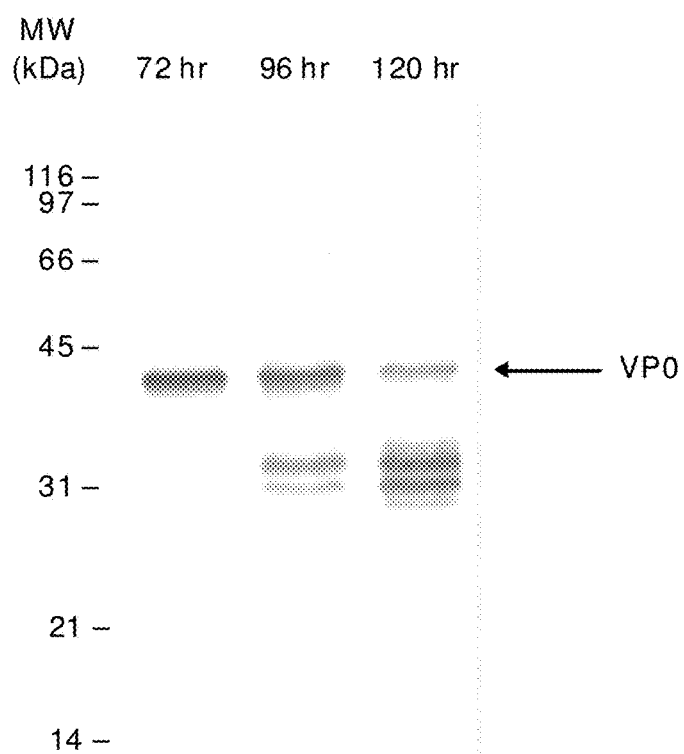

Figure 8. Pooled neutralizing sera from mice immunized with the oligomeric antigens in the supernatant of SN07 infected Sf9 cells have high titres against recombinant VP2 in ELISA.

Figure 9. Pooled neutralizing sera from mice immunized with oligomeric antigens in the supernatant of SN07 infected Sf9 cells bind more strongly to VP2 and VP0 than to VP1.
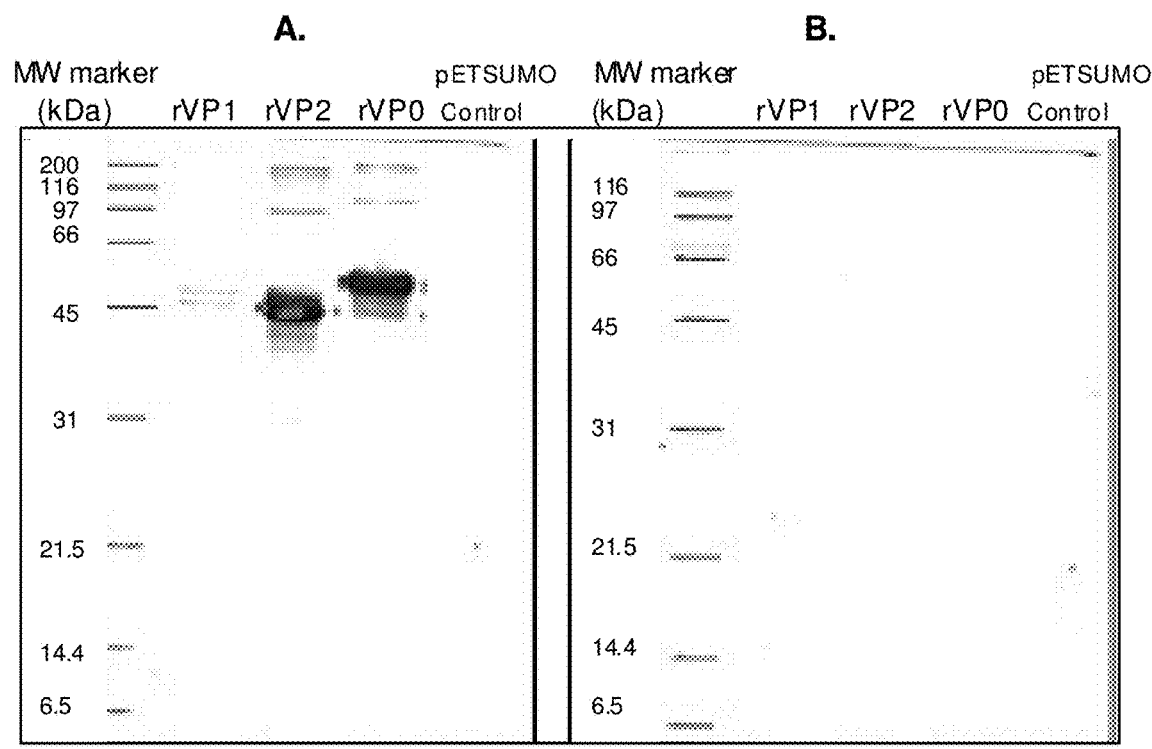
A. Probed with mice serum anti-bacSN07p3 VLPs at 1/2000 dilution.
B. Probed with mice serum anti-SF9 control cells at 1/500 dilution.

Figure 10. IRES region of the EMCV genome (SEQ ID NO:1). The IRES region represents the EMCV genomic sequence in GenBank accession number AF113968.2 ; nucleotides1666 to 2251.

Figure 11. Out framing of the EMCV start codon with the 3CD protease coding sequence; Native EMCV IRES coding sequence (SEQ ID NO:2) is compared to a mutant EMCV IRES sequence coding sequence (SEQ ID NO:3).

Native  AUGAUAAU----AUG aCu uCg Aaa gUu uAu gAu cca gaa caa

Mutant  AUGAUAAgcuugccacaacccgggauccucuagagucgacAUG acu ucg

Figure 12. Plasmid pSN01-M1.
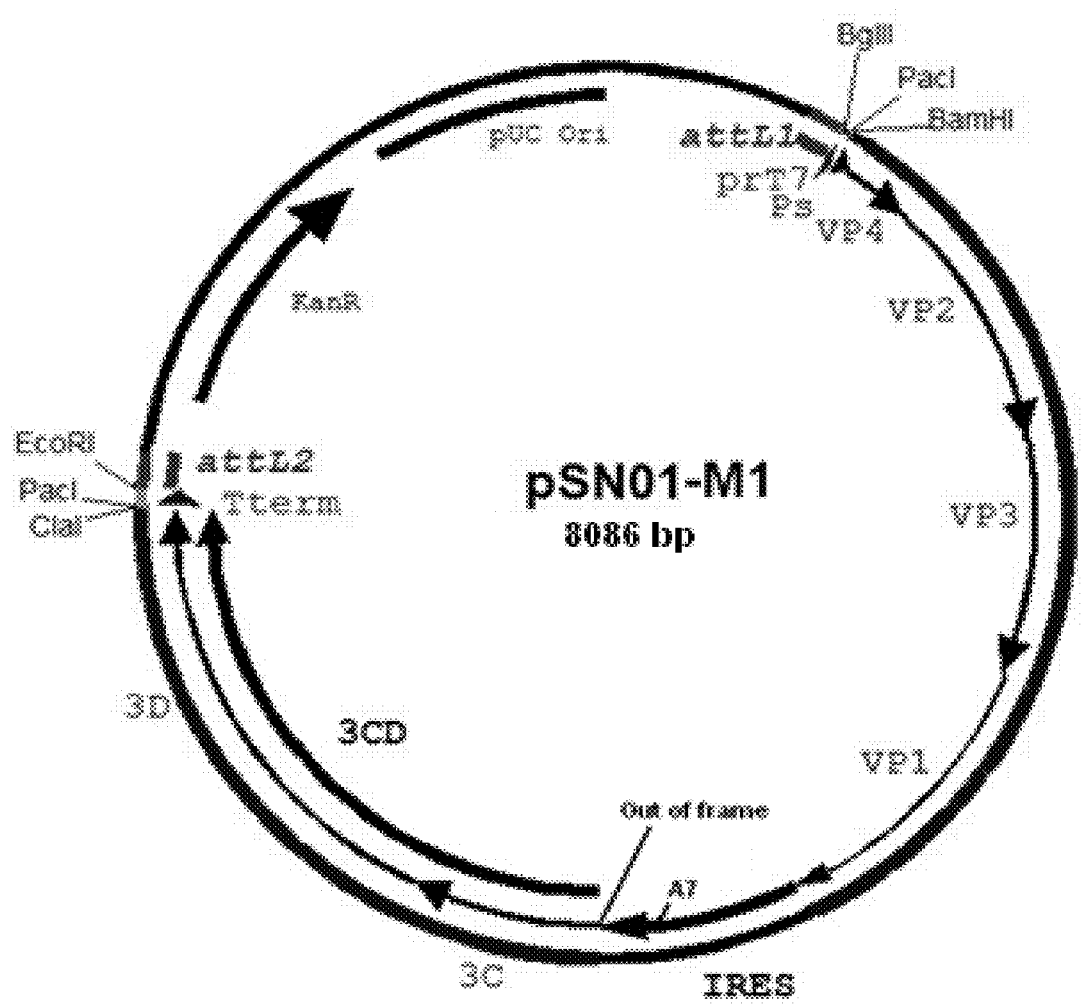

Figure 13. Plasmid pSN01-M2
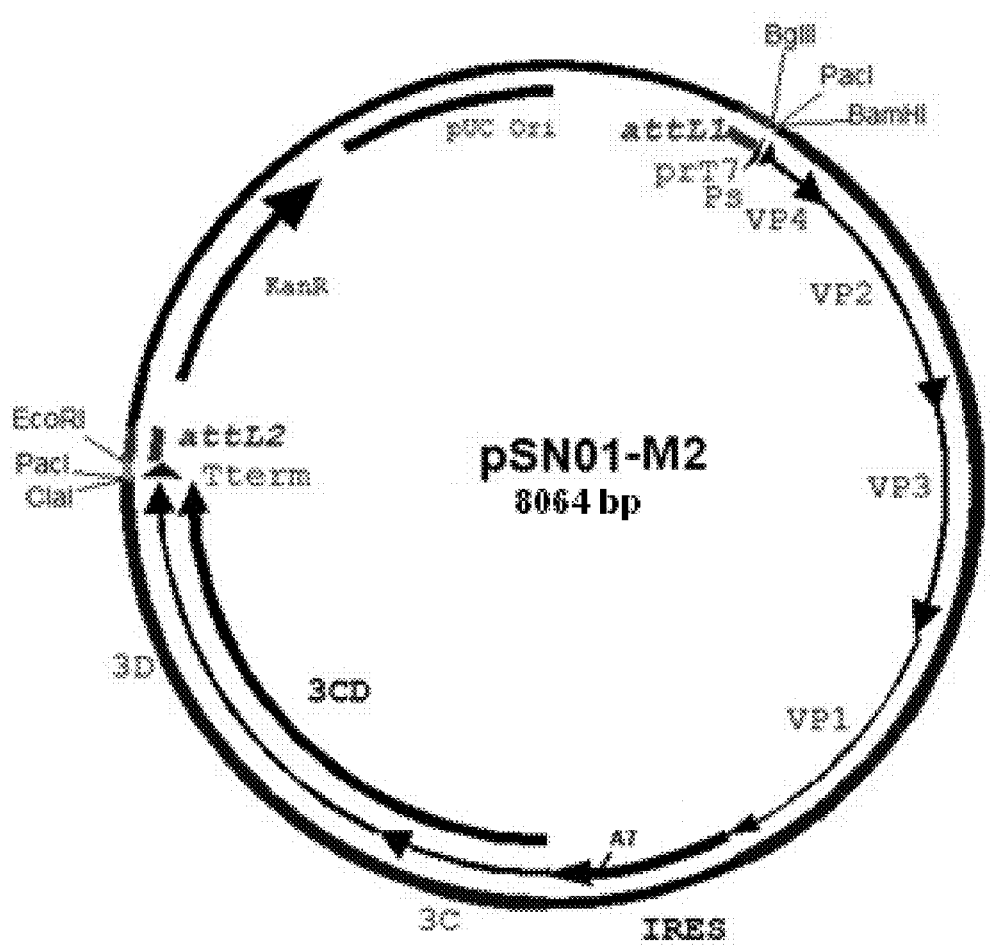

Figure 14. Plasmid pSN01-M3.
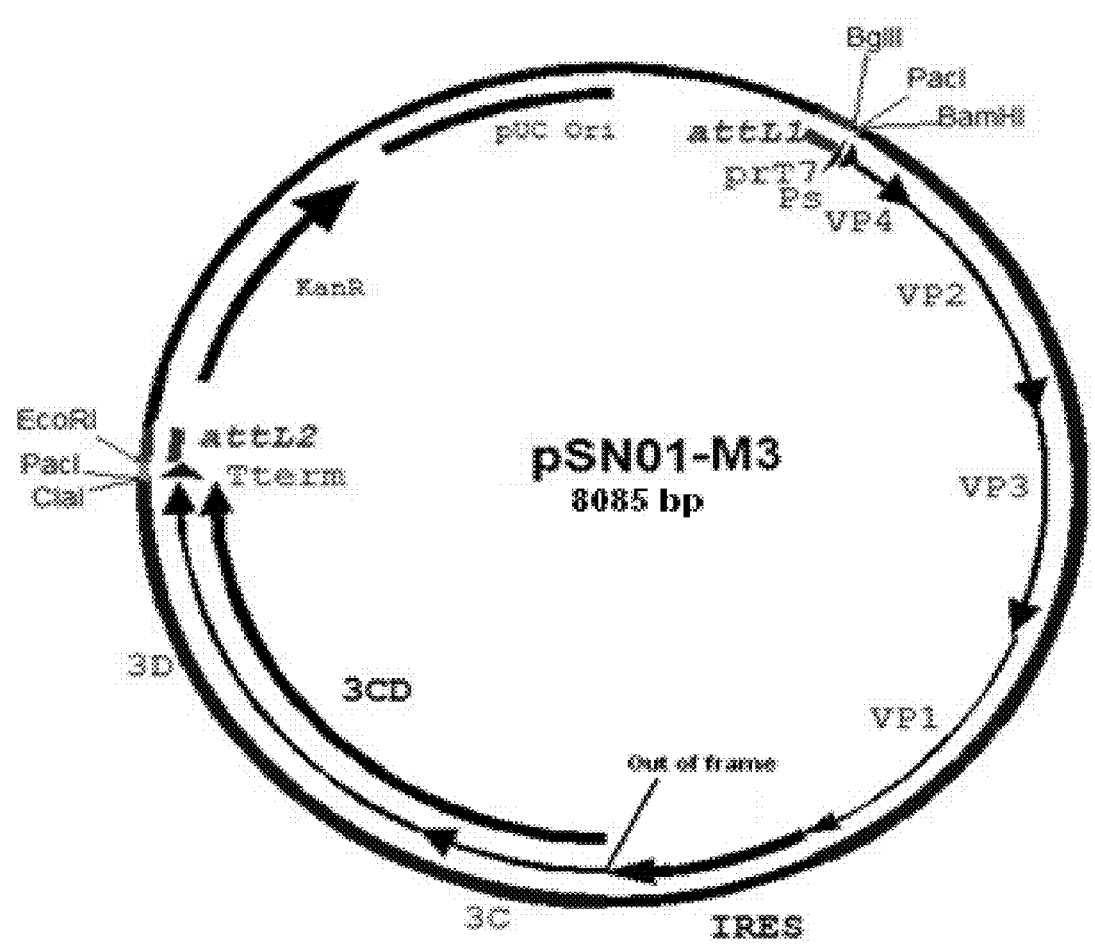

Figure 15. Comparison of expression of different recombinant baculovirus designs for expression of HEV71 VLP's.

Figure 16. Plasmid pFastBac™ HT
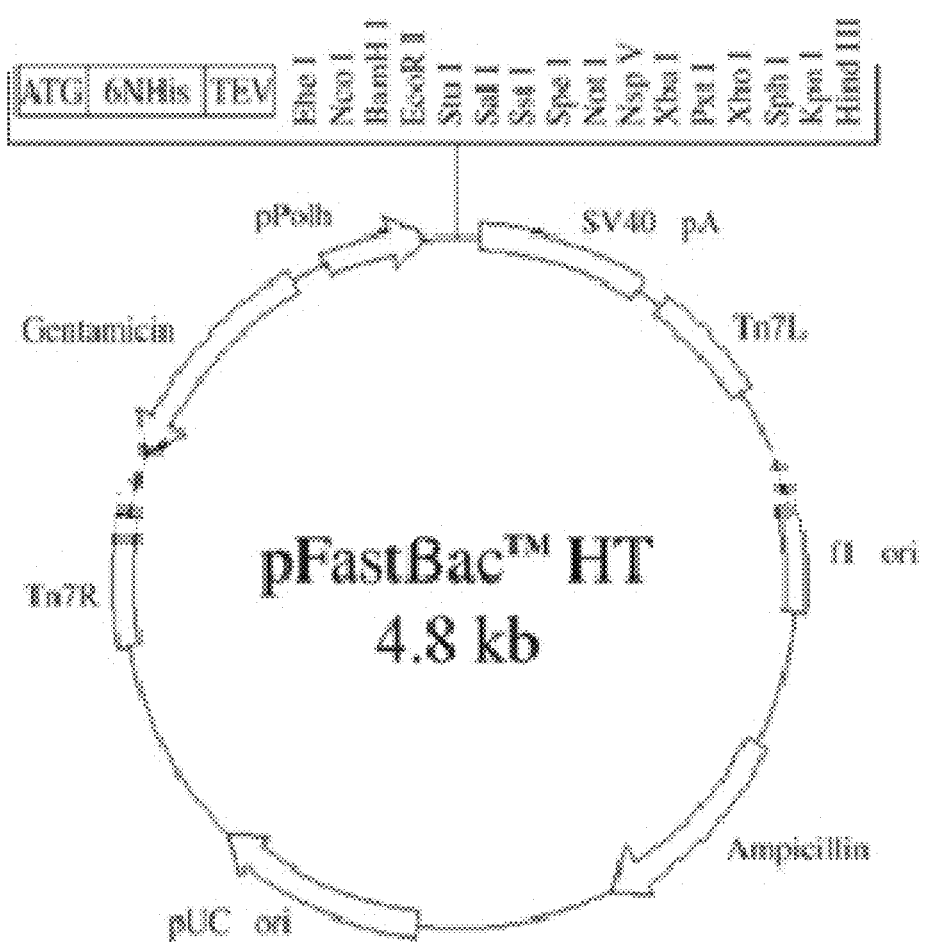

Figure 17. Prokaryotic expression construct for antigenic fusion proteins of *Human enterovirus A* and *Human enterovirus C*.

Figure 18. Antibodies from pooled neutralizing sera from mice immunized with SN07 retentate binds to all the components of HEV71 VLPs.

1. 1 ug of rEV71-VP0
2. 1 ug of rEV71-VP1
3. 1 ug of rEV71-VP2
4. 1 ug of rEV71-VP3

Pooled mice sera
Gp1/2 1:1000

Control mice sera
Gp1/2 1:1000

Figure 19. Characterization of HEV71 VLPs, pull-down of HEV71 VLPs from the culture supernatant.
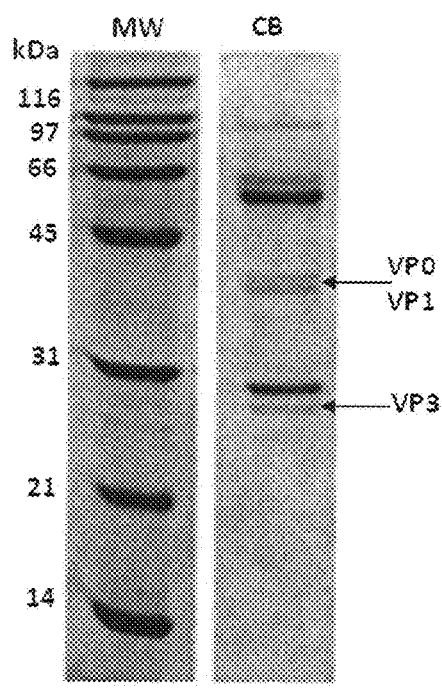

Figure 20. Analysis of affinity column (AFC) purified HEV71 VLPs.
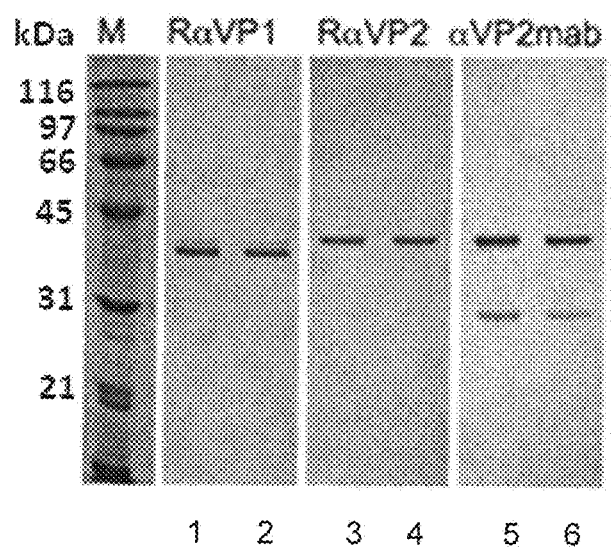

Figure 21. An electron micrograph picture of AFC purified HEV71 VLPs. The arrows point to virus-like particles.

Figure 22. *Human enterovirus C* (poliovirus-PV) VL expression.

PV EV71IRES3CD VP3 expression

PV EMCVIRES3CD VP3 expression

PV PV IRES3CD VP3 expression

1. HEV71IRES-
   lysate
2. HEV71IRES-
   supernatant
3. bacGus-lysate

1. EMCV IRES-
   lysate
2. bacGus-lysate

1. PV IRES-
   lysate
2. bacGus-lysate

Figure 23. Poliovirus-VLP VP3-VP1 ELISA.
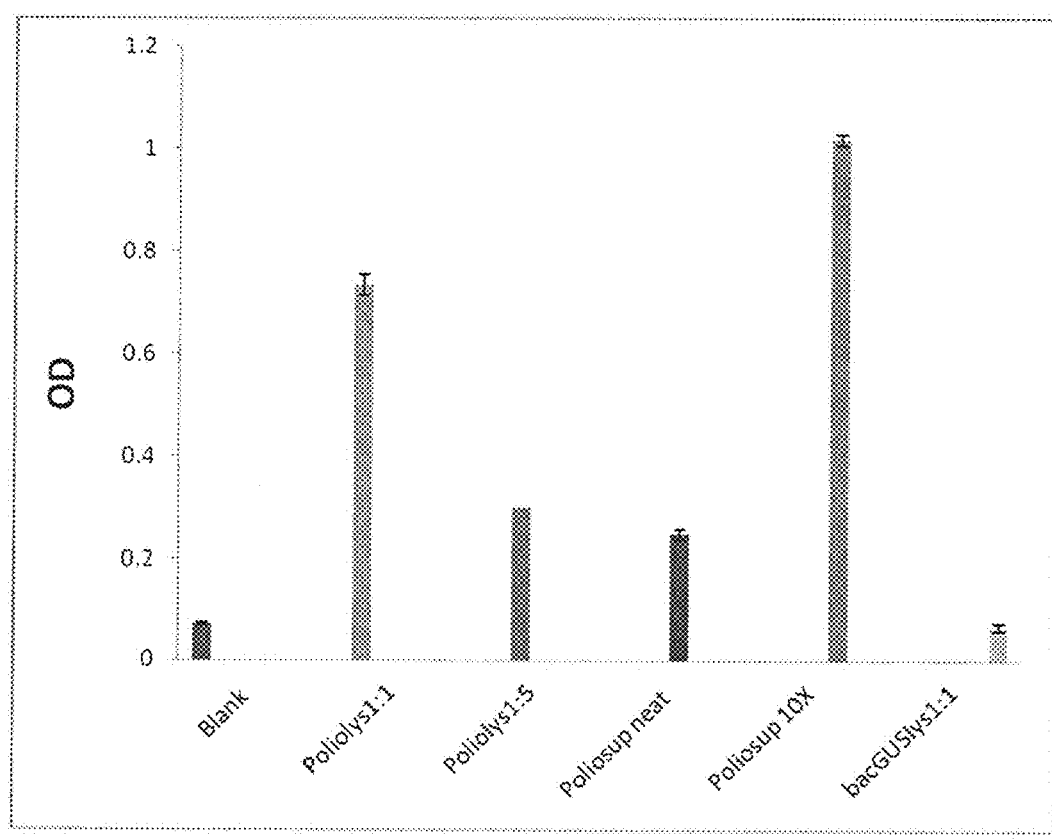

Figure 24. HEV71 VLP Expression Cassette with HEV71 IRES (P1+HEV71 IRES+3CD).

Figure 25. HEV71 VLP Expression Cassette with Poliovirus (PV) IRES (P1+PV IRES+3CD).

ANTIGENS AND VACCINES DIRECTED AGAINST HUMAN ENTEROVIRUSES

FIELD OF THE INVENTION

This invention relates to viruses of the Picornaviridae family, and in particular antigens and vaccines that may be effective in preventing and treating infections caused by such viruses.

BACKGROUND OF THE INVENTION

Picornaviruses are a diverse family of viruses which cause a number of common illnesses. Of the Picornaviridae family, viruses of the genus *Enterovirus*, which are all very closely related, are significant for the number of diseases they cause.

Viruses of the genus *Enterovirus* affect millions of people worldwide each year, and are often found in the respiratory secretions (e.g., saliva, sputum, or nasal mucus) and stool of an infected person. *Enterovirus* infects the gut, thus the derivation of their name from the root "enteric". Historically, poliomyelitis was the most significant disease caused by an *Enterovirus*, that is, *Poliovirus*. There are 62 non-polio Enteroviruses that can cause disease in humans: 23 Coxsackie A viruses, 6 Coxsackie B viruses, 28 echoviruses, and 5 other Enteroviruses. Polioviruses, as well as Coxsackie viruses and echoviruses, are spread through the fecal-oral route. Infection can result in a wide variety of symptoms ranging from mild respiratory illness (common cold), hand, foot and mouth disease, acute hemorrhagic conjunctivitis, aseptic meningitis, myocarditis, severe neonatal sepsis-like disease, and acute flaccid paralysis.

Of the picornaviruses, *Enterovirus* represents a genus of a large and diverse group of small RNA viruses characterized by a single positive-strand genomic RNA. All Enteroviruses contain a genome of approximately 7,500 bases and are known to have a high mutation rate due to low-fidelity replication and frequent recombination. After infection of the host cell, the genome is translated in a cap-independent manner into a single polyprotein, which is subsequently processed by virus-encoded proteases into the structural capsid proteins and the nonstructural proteins, which are mainly involved in the replication of the virus.

The enteroviruses are associated with several human and mammalian diseases. Serologic studies have distinguished 66 human *Enterovirus* serotypes on the basis of antibody neutralization tests. Additional antigenic variants have been defined within several of the serotypes on the basis of reduced or nonreciprocal cross-neutralization between variant strains. On the basis of their pathogenesis in humans and animals, enteroviruses were originally classified into four groups, polioviruses, Coxsackie A viruses (CA), Coxsackie B viruses (CB), and echoviruses, but it was quickly realized that there were significant overlaps in the biological properties of viruses in the different groups.

The *Enterovirus* genus includes the following ten species:
Bovine *enterovirus*
Human *enterovirus* A
Human *enterovirus* B
Human *enterovirus* C
Human *enterovirus* D
Human *rhinovirus* A
Human *rhinovirus* B
Human *rhinovirus* C
Porcine *enterovirus* B
Simian *enterovirus* A Within these ten species are there are various serotypes, for example:
*Enterovirus* serotypes HEV71, EV-76, EV-89, EV-90, EV-91, EV-92 and *coxsackievirus* A16 are found under the species Human *enterovirus* A.
Serotypes *coxsackievirus* B1 (CV-B1), CV-B2, CV-B3, CV-B4, CV-B5 (incl. swine vesicular disease virus [SVDV]), CV-B6, CV-A9, echovirus 1 (E-1; incl. E-8), E-2, E-3, E-4, E-5, E-6, E-7, E-9 (including CV-A23), E-11, E-12, E-13, E-14, E-15, E-16, E-17, E-18, E-19, E-20, E-21, E-24, E-25, E-26, E-27, E-29, E-30, E-31, E-32, E-33, *enterovirus* B69 (EV-B69), EV-B73, EV-B74, EV-B75, EV-B77, EV-B78, EV-B79, EV-B80, EV-B81, EV-B82, EV-B83, EV-B84, EV-B85, EV-B86, EV-B87, EV-B88, EV-B93, EV-B97, EV-B98, EV-B100, EV-B101, EV-B106, EV-B107, EV-B110 (from a chimpanzee) and the simian *enterovirus* SA5, are found under the species Human *enterovirus* B.
Serotypes EV-95, EV-96, EV-99, EV-102, EV-104, EV-105, and EV-109 are found under the species Human *enterovirus* C.
Serotypes EV-68, EV-70, & EV-94 are found under the species Human *enterovirus* D.
*Poliovirus* serotypes PV-1, PV-2, and PV-3 are found under the species Human *enterovirus* C.

Diseases caused by *Enterovirus* infection include poliomyelitis which is the most notable disease caused by an *Enterovirus* infection. Nonspecific febrile illness is, however, the most common presentation of an *Enterovirus* infection.

Enteroviruses are the most common causes of aseptic meningitis in children. In the United States, enteroviruses are responsible for 30,000 to 50,000 cases of meningitis. Encephalitis is a rare manifestation of an *Enterovirus* infection; when it occurs, the most frequent *Enterovirus* found to be causing the encephalitis is echovirus 9.

Pleurodynia caused by enteroviruses is characterized by severe paroxysmal pain in the chest and abdomen, along with fever, and sometimes nausea, headache, and emesis.

Pericarditis and/or myocarditis are typically caused by enteroviruses. Arrythmias, heart failure, and myocardial infarction have also been reported.

Acute hemorrhagic conjunctivitis can be caused by enteroviruses.

Hand, foot and mouth disease is a childhood illness most commonly caused by infection by Coxsackie A virus or HEV71.

A 2007 study suggested that acute respiratory or gastrointestinal infections associated with enteroviruses may be a factor in chronic fatigue syndrome.

All members of the genus *Enterovirus*, including HEV71, polioviruses and *coxsackievirus* A16 have a single stranded positive sense RNA genome which has a single open reading frame encoding a polyprotein, P1, consisting of the capsid proteins VP4, VP2, VP3 and VP1 and several non-structural proteins including the viral proteases 3C and 3CD which are responsible for cleaving the polyprotein P1 into individual capsid proteins VP1, VP3 and VP0, which VP0 is eventually cleaved into VP2 and VP4. The capsid proteins may assemble into virus like particles (VLPs).

Human *Enterovirus* 71 (HEV71) and *coxsackievirus* A16 are *Enterovirus* serotypes notable as the major causative agents for hand, foot and mouth disease (HFMD), and HEV71 is sometimes associated with severe central nervous system diseases. HEV71 was first isolated and characterized from cases of neurological disease in California in 1969. To date, little is known about the molecular mechanisms of host response to HEV71 infection, but increases in the level of mRNAs encoding chemokines, proteins involved in protein degradation, complement proteins, and pro-apoptotic proteins have been implicated.

Hand Foot and Mouth Disease (HFMD) is a common, self-limiting illness of children caused by a group of species A enteroviruses (Picornaviridae family) such as human *coxsackievirus* A16 (CVA16), *coxsackievirus* A10 (CVA10) and Human *enterovirus* A71 (HEV71). The virus is excreted in feces and is also found in pharyngeal secretions. Transmission is associated with close contact among children and through environmental contamination. The disease is characterized by an acute onset of fever with a rash on the palms, soles, buttocks, and knees, and vesicles on buccal membranes that usually resolve in 7-10 days. Only a small proportion of children with HFMD develop severe disease.

Severe disease involving primarily the neurologic and cardiovascular systems manifesting as syndromes such as meningitis, encephalitis, acute flaccid paralysis, pulmonary edema and cardiac failure generally occur only with HEV71 infection. In the Asia-Pacific Region the most devastating neurological syndrome is brainstem encephalitis, which has a mortality rate of 40-80 percent. Children with severe HFMD may take months to recover, and in some cases the neurologic damage may be permanent. Currently, there is no specific antiviral treatment for HFMD and no vaccines to prevent *Enterovirus* infection other than polio.

HEV71 was first isolated from a child who died of encephalitis in California in 1969, and first reported in 1974. Although the virus has been detected worldwide since then, the recent regional epidemics of HFMD in Asia has raised concern that more pathogenic forms of HEV71 may be emerging in the region. The first recognition of a HFMD outbreak with a high number of fatalities was in Sarawak, Malaysia in 1997. The virus associated with the outbreak then was HEV71. Taiwan reported 129,106 HFMD cases in a 1998 epidemic with 405 having severe disease with 78 deaths. Singapore reported an epidemic of 9000 cases with 7 deaths during 2000-2001, and since then has experienced recurrent epidemics every two to three years. During the first 8 months of 2008, Singapore reported 19,530 cases and one death due to HFMD. Since then HEV71 outbreaks have been reported regularly in Singapore, Thailand, Malaysia, Taiwan, Japan, Korea and Vietnam.

China reported 83,344 cases with 17 deaths in 2007, and in 2008 experienced a large outbreak in Fuyang City in Anhui Province spreading throughout many parts of China. These large outbreaks were widely covered by the press, which highlighted parental concerns about the health of their children and the social disruption from closing of schools and day care centers by public health departments in an attempt to break the chain of transmission. Since then China has reported large outbreaks annually.

With regard to disease caused by other members of the Picornaviridae family, natural infection and prevalence of polio have occurred exclusively in the human being since ancient times as an infectious disease. A large number of humans still become infected with polio every year in developing countries. Hence, the eradication of polio is an ongoing process.

Polioviruses were formerly classified as a species belonging to the genus *Enterovirus* in the family Picornaviridae. The *Poliovirus* species has been eliminated from the genus *Enterovirus*. The polioviruses are classified as serotypes, Human *Poliovirus* 1 (PV-1), Human *Poliovirus* 2 (PV-2), and Human *Poliovirus* 3 (PV-3), and are considered to be subtypes of species Human *enterovirus* C, in the genus *Enterovirus* in the family Picornaviridae. The type species of the genus *Enterovirus* was changed from *Poliovirus* to Human *enterovirus* C in 2008.

The three subtypes of species Human *enterovirus* C, PV-1, PV-2 and PV-3, are characterized by a slightly different capsid protein. Capsid proteins define cellular receptor specificity and virus antigenicity. PV-1 is the most common form encountered in nature; however, all three forms are extremely infectious and can affect the spinal cord and cause poliomyelitis.

Infection with Human *enterovirus* C has been a widespread problem and inactivated whole virus vaccines have been used for mass immunization and are currently available. Good results have been obtained with inactivated poliomyelitis vaccines which may be prepared according to a method which has been developed by Salk and has been improved later in several aspects. Generally, these vaccines contain a mixture of inactivated polio virus of strains Mahoney, MEF1 and Saukett.

Although an attenuated Human *enterovirus* C has been produced and used as an attenuated oral polio vaccine, the attenuated Human *enterovirus* C may be dangerous because of the possible reversion of pathogenicity (paralysis-based neurovirulence) in persons administered to, or in contact with, whole viruses. Hence, there is a need for a safe and effective polio vaccine which is free of such pathogenicity.

Like all enteroviruses, four different Human *enterovirus* C coat/capsid polypeptides have been identified and are designated as VP1, VP2, VP3 and VP4, which associate to form an icosahedral virus capsid. Typically, vaccination with the individual polypeptides of Human *enterovirus* C has shown that the isolated polypeptides are not capable of raising neutralizing antibodies in humans and animals (Meloen, et al., J. Gen. Virol. 45:761-763, 1979).

U.S. Pat. No. 4,508,708 teaches that individual polypeptides of polio virus and hand, foot and mouth disease virus, VP1, VP2, VP3 and VP4, are not capable of raising neutralizing antibodies in humans and animals and that, among the individual polypeptides of the hand, foot and mouth disease virus, only VP1 possesses this capability. U.S. Pat. No. 4,508,708 demonstrates that, among the Human *enterovirus* C type 2 MEF1 virion VP1, VP2 and VP3 polypeptides, only the VP3 is capable of inducing neutralizing antibodies, although the antibody titer is low. It was found, however, that VP1, VP2 and VP3 are capable of inducing neutralizing antibodies only when the immunization is carried out with a preparation containing arildone, a broad spectrum antiviral agent that has been shown to selectively inhibit replication of picornaviruses (Langford, et al. Antimicrobial Agents and Chemotherapy 28:578-580, 1985).

Thus, the problem to be solved is the preparation of an effective vaccine which provides protective immunity against a human *Enterovirus* infection, and without the use of antiviral compounds. The human enteroviruses for which protection is desired are, for example Human *enterovirus* A, including *coxsackievirus* A16 and Human *Enterovirus* 71; Human *enterovirus* B, including *coxsackievirus* B serotypes, echoviruses and *Enterovirus* serotypes; Human *enterovirus* C, including Human *Poliovirus* 1, Human *Poliovirus* 2 and Human *Poliovirus* 3; as well as Human *enterovirus* D, including EV 68.

For the purposes of the instant invention, a vaccine is understood by those skilled in the art and may further be defined as a prophylactic or therapeutic material containing antigens derived from one more pathogenic organisms which, upon administration to a human subject or animal, will stimulate active immunity and protect against infection with these or related organisms (i.e., produce protective immunity).

Furthermore, protective immunity may be well understood by those skilled in the art. Nonetheless, protective immunity comprises, at least, the induction, or elicitation of neutralizing antibodies and/or T-cell immune response which will neutralize the virus.

It is well recognized in the vaccine art, that it is unclear whether an antigen derived from a pathogen will elicit protective immunity. Ellis (Chapter 29 of Vaccines, Plotkin, et al. (eds) WB Saunders, Philadelphia, at page 571, 1998) exemplifies this problem in the recitation that "the key to the problem (of vaccine development) is the identification of that protein component of a virus or microbial pathogen that itself can elicit the production of protective antibodies . . . , and thus protect the host against attack by the pathogen."

An approach to making improved vaccines against picornaviruses would be to mimic the virus capsid structure or its components which may elicit protective antibodies such as are produced with a killed whole virus vaccine. This kind of approach is safer than a killed, inactivated or attenuated vaccine approach because there is no opportunity for reversion.

All picornaviruses share the same genomic structure, including 4 structural genes within the P1 gene: VP1, VP2, VP3, and VP4, the VP4 and VP2 being expressed together as VP0, and viral proteases within the 3C and 3D genes. The viral protease will cleave the P1 gene, thereby allowing the virus to assemble into virus like particles (VLPs), virus capsomers, complexes and/or antigens of enteroviruses.

Vaccines have been proposed with indifferent success. It has been proposed to use subunit vaccines comprising the major capsid protein, VP1, of enteroviruses, as the basis of vaccines for the prevention and treatment of *Enterovirus* infections, including HEV71 infections (Wu, et al., 2001).

With regard to prophylaxis against *Enterovirus* infection, it is possible to envisage a killed virus vaccine approach, which has been shown to elicit protective antibodies. The low virus titres achieved in general makes manufacturing of such *Enterovirus* vaccines a challenge.

The present invention pertains to vaccines including antigenic coat/capsid proteins of viruses of the Picornaviridae family and which vaccines are devoid of virus RNA which may contribute to neurovirulence. The vaccines of the invention may comprise as antigens, the polypeptides P1 or VP0, or capsid proteins (VP's), designated as VP1, VP2, VP3 and/or VP4, or immunologically or biologically active fragments thereof which elicit neutralizing antibodies against enteroviruses.

The present invention relates to vaccines in which the picornavirus antigens are present in the form of one or more picornavirus polypeptides, especially human *Enterovirus* peptides VP2, VP3 or VP0, immunogenic fragments thereof, and/or antigenic determinants thereof. The picornavirus polypeptides may be obtained by chemical synthesis or by means of recombinant DNA techniques using known human *Enterovirus* amino acid or nucleic acid sequences.

SUMMARY OF THE INVENTION

A vaccine comprising one or more immunologically active antigens comprising one or more human *Enterovirus* polypeptides selected from VP0, VP1, VP2, VP3, VP4, and immunologically active fragments thereof, such a vaccine, which elicits a protective and/or neutralizing immune response directed against a human *Enterovirus*, such a vaccine, wherein the human *Enterovirus* is selected from Human *enterovirus* A, Human *enterovirus* B, Human *enterovirus* C and Human *enterovirus* D, such a vaccine, wherein the Human *enterovirus* A is selected from Human *Enterovirus* 71 (HEV71) and *coxsackievirus* A16, wherein the Human *enterovirus* B is selected from *coxsackievirus* B and echovirus, wherein the Human *enterovirus* C is selected from Human *Poliovirus* 1, Human *Poliovirus* 2 and Human *Poliovirus* 3, and wherein the Human *enterovirus* D is EV 68, such a vaccine, wherein the vaccine comprises an immunologically active *enterovirus* VP0 polypeptide, such a vaccine, wherein the vaccine comprises an immunologically active *enterovirus* VP2 polypeptide, such a vaccine, wherein the vaccine comprises an immunologically active *enterovirus* VP3 polypeptide, such a vaccine, wherein the vaccine comprises an immunologically active *enterovirus* VP1 polypeptide, such a vaccine, wherein the vaccine comprises polypeptides from one or more *Enterovirus* species or serotype, such a vaccine, wherein the species or serotype may be Human *enterovirus* A selected from HEV71 and *coxsackievirus* A16, such a vaccine, wherein the species or serotype may be Human *enterovirus* C selected from PV-1, PV-2 and PV-3, such a vaccine, wherein the one or more immunologically active antigens comprising one or more human *Enterovirus* polypeptides selected from VP0, VP1, VP2, VP3, VP4, and immunologically active fragments thereof, are in the form of a virus-like particle, capsomer, complex and/or aggregate, such a vaccine, wherein the virus-like particle comprises an immunologically active *enterovirus* VP0 polypeptide, such a vaccine, wherein the virus-like particle comprises an immunologically active *enterovirus* VP2 polypeptide, such a vaccine, wherein the virus-like particle comprises an immunologically active *enterovirus* VP3 polypeptide, such a vaccine, wherein the virus-like particle comprises an immunologically active *enterovirus* VP1 polypeptide, a method of vaccinating a subject against an *Enterovirus* infection, comprising administering to the subject a vaccine comprising one or more immunologically active antigens comprising one or more human *Enterovirus* polypeptides selected from VP0, VP1, VP2, VP3, VP4, and immunologically active fragments thereof, in an amount effective to elicit a protective and/or neutralizing immune response when administered to the subject, such a method, wherein the vaccine comprises an immunologically active *enterovirus* VP0 polypeptide, such a method, wherein the vaccine comprises an immunologically active *enterovirus* VP1 polypeptide, such a method, wherein the vaccine comprises an immunologically active *enterovirus* VP3 polypeptide, such a method, wherein the vaccine comprises an immunologically active *enterovirus* VP2 polypeptide, such a method, wherein the one or more immunologically active antigens comprising one or more human *Enterovirus* polypeptides selected from VP0, VP1, VP2, VP3, VP4, and immunologically active fragments thereof, are in the form of a virus-like particle, capsomer, complex and/or aggregate, such a method, wherein the virus-like particle comprises an immunologically active *enterovirus* VP0 polypeptide, such a method, wherein the virus-like particle comprises an immunologically active *enterovirus* VP2 polypeptide, such a method, wherein the virus-like particle comprises an immunologically active *enterovirus* VP3 polypeptide, such a method, wherein the virus-like particle comprises an immunologically active *enterovirus* VP1 polypeptide, such a method, wherein the vaccine comprises polypeptides from one or more *Enterovirus* species or serotype, such a method, wherein the *Enterovirus* species or serotype may be Human *enterovirus* A selected from HEV71 and *coxsackievirus* A16, such a method, wherein the *Enterovirus* species or serotype may be Human *enterovirus* C selected from PV-1, PV-2 and PV-3, an expression cassette comprising a promoter operably linked to a nucleic acid encoding a human *enterovirus* P1 polypeptide, an Internal Ribosome Entry Site (IRES), and a nucleic acid encoding a human *Enterovirus* 3CD protease, such an expression cassette, wherein the polypeptide is human *enterovirus* P1, such an expression cassette, wherein the human *Enterovirus* 3CD protease processes the human *enterovirus* P1 polypeptide, such an expression cassette, wherein the processed human *enterovirus* P1 polypeptides associate to form virus like particles, capsomers, complexes and/or aggregates, such an expression cassette, wherein the human *enterovirus* P1 polypeptide comprises combinations of polypeptides selected from VP0, VP1, VP2, VP3, VP4, and immunologically active fragments thereof, such an expression cassette, wherein the human *Enterovirus* is selected from Human *enterovirus* A and Human *enterovirus* C, such an expression cassette, wherein the Human *enterovirus* A is selected from HEV71 and *coxsackievirus* A16, such an expression cassette, wherein the Human *enterovirus* C is selected from Human *Poliovirus* 1 (PV-1), Human *Poliovirus* 2 (PV-2) and Human *Poliovirus* 3 (PV-3), such an expression cassette, wherein the IRES is derived from Encephalomyocarditis virus (EMCV), such an expression cassette, wherein the IRES derived from Encephalomyocarditis virus (EMCV) has been genetically modified to reduce IRES activity, such an expression cassette, wherein the IRES derived from EMCV has been genetically modified by adding one nucleotide (A7) to the A6 bifurcation loop in the JK segment, such an expression cassette, wherein the IRES is derived from a human *Enterovirus*, such an expression cassette, wherein the promoter is a eukaryotic promoter, such an expression cassette, wherein the eukaryotic promoter is a polyhedrin promoter, such an expression cassette, wherein the promoter is operably linked to a nucleic acid encoding a Human *enterovirus* A P1 polypeptide, an EMCV IRES, and a Human *enterovirus* A 3CD protease, such an expression cassette, wherein the EMCV IRES has been mutated to reduce IRES activity, such an expression cassette, wherein the promoter is operably linked to a nucleic acid encoding a Human *enterovirus* A P1 polypeptide, an HEV71 IRES, and a Human *enterovirus* A 3CD protease, such an expression cassette, wherein the promoter is operably linked to a nucleic acid encoding a Human *enterovirus* A P1 polypeptide, a Human *enterovirus* C IRES, and a Human *enterovirus* A 3CD protease, such an expression cassette, wherein the promoter is operably linked to a nucleic acid encoding a Human *enterovirus* C P1 polypeptide, a Human *enterovirus* C IRES, and a Human *enterovirus* C 3CD protease, such an expression cassette, wherein the promoter is operably linked to a nucleic acid encoding a Human *enterovirus* C P1 polypeptide, an HEV71 IRES, and a Human *enterovirus* C 3CD protease, such an expression cassette, wherein the promoter is operably linked to a nucleic acid encoding a Human *enterovirus* C P1 polypeptide, an EMCV IRES, and a Human *enterovirus* C 3CD protease, such a method of making a vaccine comprising introducing an VLP expression cassette into a host cell, culturing the host cell for a period of time sufficient to produce the polypeptides of the expression cassette and recovering human *Enterovirus* polypeptides from the host cell and/or culture supernatant, such a method, wherein the host cell is a eukaryotic cell, such a method, wherein the eukaryotic cell is selected from insect cells, mammalian cell lines and yeast cells, such a method, wherein the insect cells are selected from *Spodoptera frugiperda, Trichoplusia ni, drosophila*, and mosquito cells derived from *Aedes albopictus*, such a method, wherein the mammalian cell lines are selected from CHO, HEK 293, COS-1, HeLa, Vero and NIH3T3.

Figure 1:
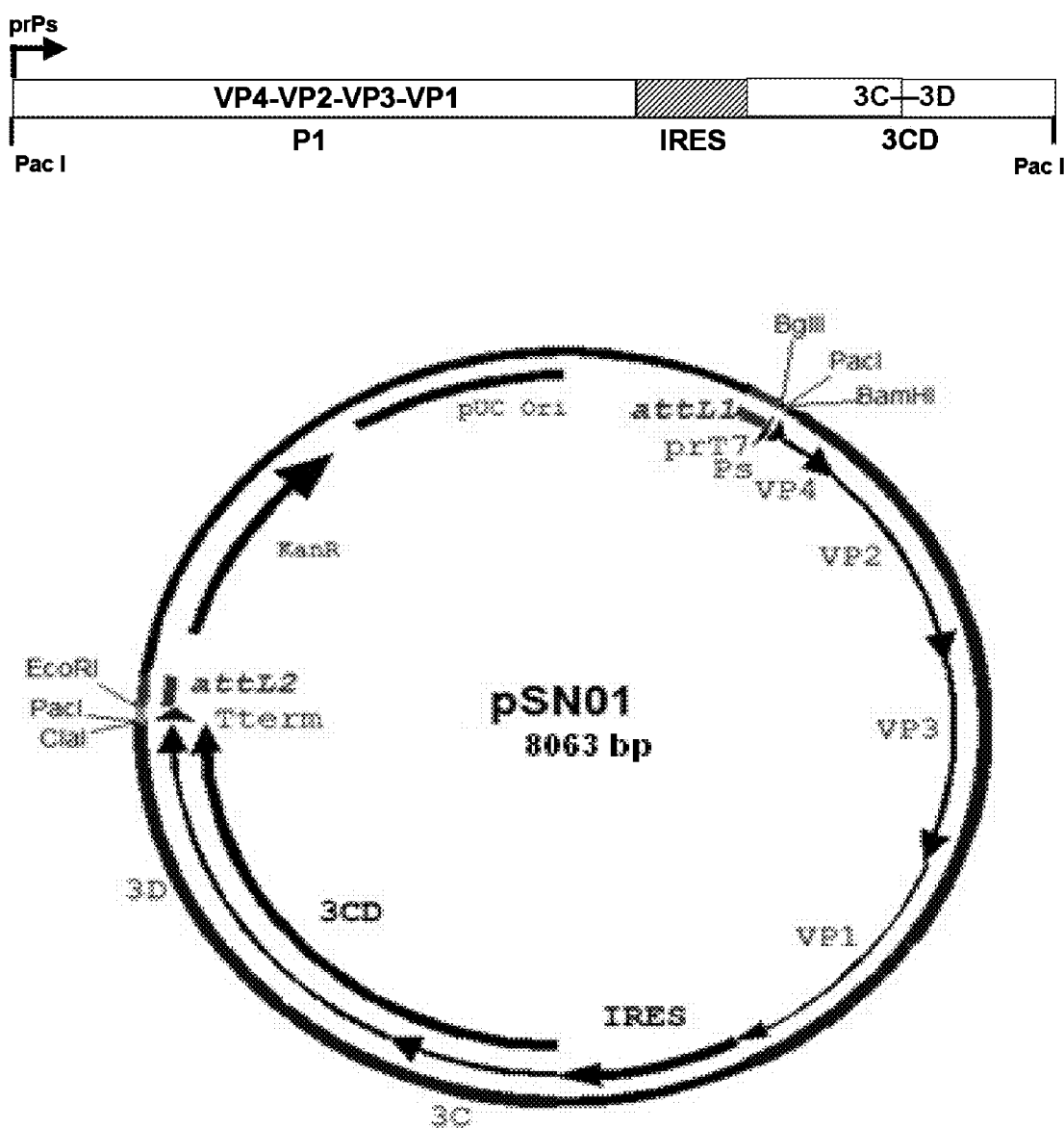
FIG. 1, HEV71 VLP expression cassette [P1+IRES+3CD] and the pSN01 plasmid.

The immunogen was prepared in Freund's Complete Adjuvant (FCA) or Freund's Incomplete Adjuvant (FIA) and administered via subcutaneous injection (sc) or intraperitoneal injection (ip).

FIG. 7. Immunoblots probed with rabbit polyclonal antisera against VP0 (arrow) at 3 different times of harvest.

FIG. 8. Pooled neutralizing sera from mice immunized with the oligomeric antigens in the supernatant of SN07 infected Sf9 cells have high titres against recombinant VP2 in ELISA.

FIG. 9. Pooled neutralizing sera from mice immunized with oligomeric antigens in the supernatant of SN07 infected Sf9 cells bind more strongly to VP2 and VP0 than to VP1.

FIG. 10. EMCV IRES (SEQ ID NO:1) region of the EMCV genome.

FIG. 11. Out framing of the EMCV start codon with 3CD protease coding sequence; native IRES sequence (SEQ ID NO:2) versus mutant IRES sequence (SEQ ID NO:3).

FIG. 12. Plasmid pSN01-M1.

FIG. 13. Plasmid pSN01-M2

FIG. 14. Plasmid pSN01-M3.

FIG. 15. Comparison of expression of different recombinant baculovirus designs for expression of HEV71 VLP's.

FIG. 16. Plasmid pFastBac™ HT.

FIG. 17. Prokaryotic expression construct for antigenic fusion proteins of Human *enterovirus* A and Human *enterovirus* C.

FIG. 18. Antibodies from pooled neutralizing sera from mice immunized with SN07 retentate binds to all the components of HEV71 VLPs.

FIG. 19. Characterization of HEV71 VLPs, pull-down of HEV71 VLPs from the culture supernatant. The VLP components (VP0, VP1 and VP3) are visible in the Coomassie stained SDS-PAGE gel. (MW—molecular weight marker; CB—Coomassie blue staining)

FIG. 20. Analysis of affinity column (AFC) purified HEV71 VLPs. AFC was prepared with a neutralizing monoclonal antibody (EV18/4/D6-1/F1/G9), which monoclonal antibody was developed using a SN07 retentate. The eluted fraction was analyzed by Western blotting. The eluted fraction in Lanes 1 and 2, probed using an anti-VP1 antibody, shows that VP1 is present in the AFC purified VLPs. The eluted fraction in Lanes 3 and 4, probed using an anti-VP2 antibody, shows that VP2 is also present in the AFC purified VLPs. The eluted fraction in Lanes 5 and 6, probed using an anti-VP2 monoclonal antibody, shows that VP2 is present in the AFC purified VLPs.

FIG. 21. An electron micrograph picture of AFC purified HEV71 VLPs. AFC was prepared with a neutralizing monoclonal antibody (EV18/4/D6-1/F1/G9), which monoclonal antibody was developed using a SN07 retentate. The eluted fraction was analyzed by Western blotting (FIG. 20) and electron microscopy. The arrows point to virus-like particles.

FIG. 22. Human *enterovirus* C (*poliovirus*-PV) VLP expression. Three different expression cassettes to generate *poliovirus* VLPs were constructed. The expression cassettes all comprise a *poliovirus* P1 polypeptide and differed with respect to the IRES. which IRES directs the expression of a *Poliovirus* 3CD protease. Recombinant baculoviruses harboring the *poliovirus* VLP expression cassettes were tested. Lysates from the baculovirus infected cells were harvested on day 3 post infection and expression of the *poliovirus* VP3 was evaluated using rabbit anti-PVP3 antibodies (1:2000).

FIG. 23. *poliovirus*-VLP VP3-VP1 ELISA. To demonstrate *poliovirus* VLP generation, a two sites ELISA was performed using lysates and supernatants from recombinant baculoviruses carrying a *poliovirus* VLP expression cassette wherein the *Poliovirus* 3CD protease is under the control of a *poliovirus* IRES. Purified rabbit anti-*poliovirus* VP3 antibodies were used as capture antibodies. *poliovirus* VLPs were detected using mouse anti-VP1 monoclonal antibodies.

FIG. 24. HEV71 VLP expression cassette with HEV71-IRES and HEV71 3CD protease.

FIG. 25. HEV71 VLP expression cassette with PV-IRES and HEV71 3CD protease.

DETAILED DESCRIPTION OF THE INVENTION

The invention provides virus like particles (VLPs), virus capsomers, aggregates, and complexes of antigens from viruses of the Picornaviridae family as an immunogenic composition and/or vaccine for the protection against and/or treatment of a picornavirus infection. Representative examples may include an *Enterovirus*, a *Coxsackie virus*, and a *Poliovirus*.

The invention in another aspect provides virus proteins for example, a P1 protein or a combination of picornavirus VP0 proteins, VP1 proteins, VP2 proteins, VP3 proteins, and/or VP4 proteins, or immunologically or biologically active fragments thereof, which elicit neutralizing antibodies. The invention includes fusion-proteins comprising the aforementioned virus proteins and/or fragments thereof, which fusion proteins are immunologically active or biologically active to elicit production of neutralizing antibodies which are protective.

In an embodiment, an *Enterovirus* antigen may be a combination of *Enterovirus* coat/capsid proteins, or immunologically active fragments thereof. The virus coat/capsid proteins may be any combination of VP0, VP1, VP2, VP3 and/or VP4 proteins, and may take the form of a virus-like particle (VLP), capsomer, complex and/or aggregate. The combination may be in the form of a fusion protein.

The invention in an additional aspect includes a method for production of Picornaviridae virus like particles (VLPs), capsomers, complexes and/or aggregates which may include the steps of: (i) constructing an expression cassette operably linked to a promoter comprising one or more nucleic acids which each encode a picornavirus protein, for example, a P1 protein or a combination of picornavirus VP0 protein, VP1 protein, VP2 protein, VP3 protein, and/or a VP4 protein, which is/are operably linked to an internal ribosome entry site (IRES), which IRES is operably linked to a 3C or 3CD protease; (ii) transfecting or transforming a suitable host cell with the expression cassette; (iii) culturing the host cells under conditions in which virus like particles (VLPs) and/or capsomers and/or antigens are produced by the cell after expression of the nucleic acids comprised in the cassette.

A nucleic acid or recombinant DNA molecule may be obtained whereby open reading frames which encode *coxsackievirus* A16, HEV71, Human *enterovirus* C (human polioviruses PV1, PV2 and/or PV3), EV 68, or any other picornavirus proteins and proteases may be amplified by PCR amplification using suitably designed primers complementary to nucleic acid sequences of *coxsackievirus* A16, HEV71 or Human *enterovirus* C or any other picornavirus. Suitable primers may be designed according to standard techniques from publicly available nucleic acid sequences of enteroviruses, including *coxsackievirus* A16, HEV71 and Human *enterovirus* C or any other picornavirus. Complete genome sequences are available in GenBank and are accessible at the National Center for Biotechnology Information (NCBI).

In an embodiment, a picornavirus P1 protein, or any *enterovirus* P1 protein, is expressed as a polypeptide which is subsequently cleaved by the 3C or 3CD protease into VP0, VP1 and VP3 virus protein, or immunologically or biologically active fragments thereof, which *Enterovirus* proteins elicit neutralizing antibodies directed against enteroviruses. The VP0 protein may be further cleaved into VP2 and VP4 proteins, or immunologically or biologically active fragments thereof which elicit neutralizing antibodies directed against enteroviruses. The virus proteins may self-assemble into VLPs, capsomers and/or aggregates of *Enterovirus* proteins. Further it will be appreciated that the protease genes may be included in the same DNA recombinant molecule of the VLP expression cassette or in different DNA recombinant molecules, and/or expressed from different promoters or translation elements.

Recombinant DNA molecules and nucleic acids of the VLP expression cassettes may be devised whereby open reading frames which encode picornavirus structural proteins or proteases may be obtained by PCR amplification using suitably designed primers complementary to nucleic acid sequences of human picornaviruses.

In a further embodiment, the recombinant DNA molecule may encode a fusion protein having at least two *Enterovirus* structural proteins, or portions thereof, which are expressed as a single polypeptide antigen.

The present invention encompasses a VLP expression cassette which harbors the gene sequences for *Enterovirus* structural proteins (P1 region) with a protease (3CD) which is necessary for the processing of P1 proteins into the proteins of the virus capsid, thus allowing the self-assembly of *enterovirus* VLPs. The expression cassette is a bicistronic vector which uses a promoter upstream of the nucleic acid coding sequence for an *enterovirus* P1 protein. Downstream from the cistron encoding the P1 protein is an internal ribosome entry site (IRES) sequence followed by the cistron containing a nucleotide sequence encoding the 3CD protease.

Expression of the P1 region and the 3CD protease proceeds from a single bicistronic message wherein the 3CD protease gene is translated in a cap-independent fashion under the control of the IRES. It is observed that expression of the protease 3CD may be moderately toxic leading to premature death of the host cells, thereby lowering the yield of the *Enterovirus* capsid proteins and VLPs. The activity of the protease may be reduced while maintaining the high level of P1 protein expression from the cassette. Different IRESs and IRES sequences comprising mutations were inserted into the expression cassettes to control expression/activity of the 3CD protease and to identify effective IRES to properly process the P1 without being toxic to the cell. For efficient production of VLPs, a number of recombinant baculoviruses which have the complete P1 coding sequence and the complete 3CD protease coding sequence whose expression is under the control of IRESs from different species or serotypes of viruses, were tested for efficient production of VLPs.

For example, the expression cassette of invention may comprise a promoter which is operably linked to a nucleic acid encoding a Human *enterovirus* A P1 polypeptide, an EMCV IRES, and a Human *enterovirus* A 3CD protease.

The expression cassette of invention may comprise a promoter which is operably linked to a nucleic acid encoding a Human *enterovirus* A P1 polypeptide, a Human *enterovirus* C IRES, and a Human *enterovirus* A 3CD protease.

The expression cassette of invention may comprise a promoter which is operably linked to a nucleic acid encoding a Human *enterovirus* C P1 polypeptide, an HEV71 IRES, and a Human *enterovirus* C 3CD protease.

Furthermore, the expression cassette of invention may comprise a promoter which is operably linked to a nucleic acid encoding a Human *enterovirus* C P1 polypeptide, an EMCV IRES, and a Human *enterovirus* C 3CD protease.

Moreover, making truncations and mutations of the 3CD protease in the expression cassette which comprises efficient IRES may achieve maximum yield of VLPs. For example, the Glycine of the HEV71 3C protease which is amino acid 1671 of GenBank accession number DQ341362.1 is changed to an Alanine using site directed mutagenesis for the expression of mutant HEV71 3C and subsequent processing of an HEV71 P1 polypeptide.

Counter to conventional wisdom in the art with respect to the goal of achieving high levels of expression and activity of a protein from an expression cassette, in an embodiment, the instant invention actually seeks to reduce the activity of a protein to achieve a maximum protein yield. Mutation of the IRES or 3C protease nucleic acid to reduce activity unexpectedly results in an increased yield of *Enterovirus* capsid proteins and VLPs.

The expression cassettes may be cloned into suitable vectors and transformed/transfected into appropriate host cells for expression and purification of antigens for vaccines and protection against infections from picornaviruses, including enteroviruses.

The expression cassettes encoding picornavirus antigens may be comprised in plasmids which may be transfected into eukaryotic host cells and expressed under the appropriate growth conditions. Suitable eukaryotic expression systems are known to those skilled in the art and include inducible expression systems and appropriate eukaryotic host cells.

Mammalian cell expression vectors comprising an expression cassette of the invention include those which may be transiently transfected into host cells and cell lines. Moreover, mammalian cell expression vectors may be vectors which are stably maintained within the host cell following transfection.

Furthermore, mammalian cell expression vectors may include vectors which are stably or transiently transfected into mammalian host cells or cell lines wherein expression of the protein of interest is induced by the addition of an inducing agent into the culture medium. Mammalian host cells and cell lines include, for example, CHO, HEK 293, COS-1, HeLa, Vero and NIH3T3 cells. It will also be appreciated that other eukaryotic host cells may include yeast cells or other mammalian cell lines.

The expression cassette may be contained in recombinant viruses which may transfect the host cell. Suitable viruses that may be used for this purpose include baculovirus, vaccinia, sindbis virus, SV40, Sendai virus, retrovirus and adenovirus. Suitable host cells may include host cells that are compatible with the above viruses and these include insect cells such as *Spodoptera frugiperda* (e.g. Sf9 cells) *Trichoplusia ni*, CHO cells, chicken embryo fibroblasts, BHK cells, human SW13 cells, *drosophila*, mosquito cells derived from *Aedes albopictus*.

The expression cassette comprising *Enterovirus* nucleic acids may be introduced into an appropriate host cell by means known to those skilled in the art. The host cells are propagated and cultured under conditions which allow expression of *Enterovirus* genes and proteins.

A gene encoding an *enterovirus* VP2 protein, or immunologically or biologically active fragments thereof which elicit neutralizing antibodies against enteroviruses, may be inserted in a plasmid containing a suitable promoter and expressed in a host cell. The produced *enterovirus* VP2 protein will be isolated and used as the basis of an immunogenic composition for use as a vaccine or for diagnostic use.

A gene encoding an *enterovirus* VP4 protein, or immunologically or biologically active fragments thereof which elicit neutralizing antibodies against enteroviruses, may be inserted in a plasmid containing a suitable promoter and expressed in a host cell. The produced *enterovirus* VP4protein will be isolated and used as the basis of an immunogenic composition for use as a vaccine or for diagnostic use.

A gene encoding an *enterovirus* VP0 protein, or immunologically or biologically active fragments thereof which elicit neutralizing antibodies against enteroviruses, may be inserted in a plasmid containing a suitable promoter and expressed in a host cell. The produced *enterovirus* VP0 protein will be isolated and used as the basis of an immunogenic composition for use as a vaccine or for diagnostic use.

A gene encoding an *enterovirus* VP0 protein may be operably linked to a suitable promoter and inserted into a plasmid, which plasmid exhibits an *Enterovirus* protease linked to a suitable promoter to provide a doubly recombinant plasmid, which doubly recombinant plasmid may ultimately be expressed in a eukaryotic or prokaryotic cell expression system.

Suitable vectors for the cloning of genes and expression of *Enterovirus* polypeptide antigens include cosmids or plasmids. Suitable expression systems include prokaryotic expression systems known to those skilled in the art and prokaryotic host cells, including *E. coli*, transformed with the cosmids or plasmids for expression of proteins in prokaryotic cells.

Suitable expression systems include eukaryotic expression systems known to those skilled in the art and eukaryotic host cells transformed with plasmids for expression of proteins in various eukaryotic host cells and cell lines.

Moreover, the *Enterovirus* polypeptide antigens may be obtained from host cells or culture supernatants by means known to those skilled in the art.

The *enterovirus* VLPs, capsomers, antigens, immunologically active components thereof, and/or aggregates thereof, may be obtained from transfected and/or transformed host cells, or host cell culture medium, supernatants and lysates by any suitable means of purification known to those skilled in the art. Isolation of proteins released into the culture medium is a facile method of obtaining *enterovirus* VLPs, capsomers, antigens and/or aggregates. The *enterovirus* VLPs, capsomers, antigens, immunologically active components thereof, and/or aggregates thereof, may be further concentrated and purified by means known to those skilled in the art.

The invention in another aspect includes a vaccine containing picornavirus antigens, such as *Enterovirus* antigens, VLPs and/or capsomers in combination with a suitable adjuvant. The picornavirus antigens, immunologically active fragments thereof, VLPs and/or capsomers may be combined with any suitable adjuvant such as Modified Vaccinia Virus, ISCOMS, alum, aluminum hydroxide, aluminum phosphate, Freund's Incomplete or Complete Adjuvant, Quil A and other saponins or any other adjuvant as described for example in Vanselow (1987) S. Vet. Bull. 57 881-896.

The meaning of the terms "aluminum phosphate" and "aluminum hydroxide" as used herein includes all forms of aluminum hydroxide or aluminum phosphate which are suitable for adjuvanting vaccines.

Moreover, picornavirus antigens may be prepared by chemical synthesis of polypeptides based on the publicly available nucleic acid or protein sequences of human *Poliovirus* or by chemical synthesis.

In an aspect, the invention provides a vaccine comprising one or more Human *enterovirus* C antigen(s). As used herein the expression "*Poliovirus* antigen" or "Human *enterovirus* C antigen" refers to any antigen capable of stimulating neutralizing antibodies to Human *enterovirus* C. The virus antigen may comprise a coat/capsid protein, or fragments thereof, antigenic determinants, and/or other Human *enterovirus* C proteins.

The invention in one aspect includes Human *enterovirus* C virus subunit vaccines comprising a single Human *enterovirus* C virus coat/capsid protein as an antigen. More specifically the invention pertains to vaccines comprising a Human *enterovirus* C VP2 coat/capsid protein, or immunogenic fragment thereof, as antigen.

The invention in another aspect includes a vaccine comprising Human *enterovirus* C virus like particles (VLPs), capsomers, complexes and/or aggregates, comprising Human *enterovirus* C VP1, VP2, VP3 and/or VP4, or VP0 proteins.

A recombinant DNA molecule may be obtained whereby nucleic acids comprising open reading frames which encode Human *enterovirus* C structural proteins or proteases may be obtained by PCR amplification using suitably designed primers complementary to nucleic acid sequences of human Human *enterovirus* C. Suitable primers may be designed according to standard techniques from publicly available nucleic acid sequences of Human *enterovirus* C, such as those complete genome sequences available in GenBank and accessible at the National Center for Biotechnology Information (NCBI). Accession numbers for the complete genome of the Human *enterovirus* C *Poliovirus* type I genome include V01149 and V01150.

The expression cassettes of the invention may comprise nucleic acids which encode a Human *enterovirus* C P1 polypeptide. The P1 polypeptide is processed (cleaved) by the 3CD protease translated under the control of the IRES of the expression cassette to yield VP1, VP3 and/or VP0 polypeptides. Combinations of VP0, VP1 and VP3 may self-associate into virus-like particles.

The Human *enterovirus* C polypeptide antigen may comprise a Human *enterovirus* C coat/capsid VP2 protein, a product of further processing of VP0, in combination with another *poliovirus* VP0, VP1, VP3 and/or VP4 coat/capsid proteins. The combination of Human *enterovirus* C coat/capsid proteins may take the form of a virus-like particle (VLP), capsomer, complex and/or aggregate.

A gene encoding a Human *enterovirus* C coat/capsid VP2 protein may be inserted into a plasmid containing a suitable promoter and expressed in a host cell, the protein isolated and used as the basis of an immunogenic composition for use as a vaccine. Furthermore, the gene encoding human *poliovirus* VP2 protein may be inserted into a plasmid containing a suitable promoter and expressed in a host cell, the protein isolated, and used as the basis of an immunogenic composition for use as a vaccine.

A gene encoding a Human *enterovirus* C coat/capsid VP4 protein may be inserted into a plasmid containing a suitable promoter and expressed in a host cell, the protein isolated and used as the basis of an immunogenic composition for use as a vaccine. Furthermore, the gene encoding human *poliovirus* VP4 protein may be inserted into a plasmid containing a suitable promoter and expressed in a host cell, the protein isolated, and used as the basis of an immunogenic composition for use as a vaccine.

A gene encoding a Human *enterovirus* C coat/capsid VP0 protein may be inserted into a plasmid containing a suitable promoter and expressed in a host cell, the protein isolated and used as the basis of an immunogenic composition for use as a vaccine. Furthermore, the gene encoding human *poliovirus* VP0 protein may be inserted into a plasmid containing a suitable promoter and expressed in a host cell, the protein isolated, and used as the basis of an immunogenic composition for use as a vaccine.

The invention encompasses a vaccine comprising one or more immunologically active antigens comprising one or more Human *enterovirus* C VP0, VP1, VP2, VP3, VP4 polypeptides, and immunologically active fragments thereof, which vaccine elicits a protective and/or neutralizing immune response directed against a human *Enterovirus*.

In an embodiment, the expression cassette consists essentially of a nucleic acid encoding a Human *enterovirus* C P1 polyprotein, an IRES and an *Enterovirus* 3CD protease under the translational control of the IRES, which protease processes the Human *enterovirus* C P1 polyprotein into structural capsid proteins.

In another aspect, the invention provides a vaccine comprising Human *enterovirus* A antigen(s), derived from a P1 polyprotein including, VP2, VP4 and/or VP0 proteins, and/or biologically or immunologically active fragments thereof. The Human *enterovirus* A antigens may be derived from HEV71 and/or *coxsackievirus* A16. The HEV71 antigen may be a single human *Enterovirus* virus coat/capsid protein. In particular, the HEV71 antigen may be an HEV71 P1 polyprotein, a VP4, VP2 or VP0 polypeptide, or a fragment thereof, which elicits an immune response upon administration to a human.

In an embodiment, the Human *enterovirus* A antigen may be a combination of Human *enterovirus* A coat/capsid proteins, or immunologically active fragments thereof. For example, the Human *enterovirus* A antigen may comprise a *poliovirus* VP2 protein, in combination with another *Poliovirus* coat/capsid proteins selected from VP1, VP3 and/or VP4 polypeptides. The combination of a VP2 polypeptide with other *Poliovirus* coat/capsid proteins may take the form of a virus-like particle (VLP), capsomer, complex and/or aggregate. The combination may be in the form of a fusion protein.

More specifically the invention pertains to vaccines comprising a Human *enterovirus* A VP2 coat/capsid protein, or immunogenic fragment thereof, as antigen.

The invention in another aspect includes a vaccine comprising Human *enterovirus* A virus like particles (VLPs) and/or capsomers comprising VP1, VP2, VP3 and/or VP4, or VP0 Human *enterovirus* A proteins.

A recombinant DNA molecule may be obtained whereby open reading frames which encode Human *enterovirus* A structural proteins and/or proteases may be amplified by PCR amplification using suitably designed primers complementary to nucleic acid sequences of Human *enterovirus* A. Suitably designed primers may be designed according to standard techniques from publicly available nucleic acid sequences of HEV71. Accession numbers for the complete genome of HEV71 include DQ341362, AB204852, AF302996 and AY465356.

A recombinant DNA molecule may be obtained whereby open reading frames which encode Human *enterovirus* A P1, VP1, VP2, VP3 and/or VP4, or VP0 proteins, and immunologically active fragments thereof, and proteases, may be obtained by PCR amplification using suitably designed primers complementary to nucleic acid sequences of Human *enterovirus* A.

In an aspect of the invention, a Human *enterovirus* A P1 protein is expressed to form a polyprotein or polypeptide which is subsequently cleaved by the 3C or 3CD protease into VP0, VP1 and VP3 proteins. VP0 proteins may be further cleaved into VP2 and VP4 proteins. The *Enterovirus* proteins may self-assemble into VLPs, capsomers, complexes and/or aggregates of *Enterovirus* proteins. Further it will be appreciated that the non-structural genes and the protease genes may be included in the same DNA recombinant molecule or in different DNA recombinant molecules, and or expressed from different promoters or translation elements.

The expression cassettes of the invention may comprise nucleic acids which encode a Human *enterovirus* A P1 polypeptide. The P1 polypeptide is processed (cleaved) by the 3CD protease translated under the control of the IRES of the expression cassette to yield VP1, VP3 and VP0 polypeptides and immunologically active fragments thereof. Combinations of VP0, VP1 and VP3 polypeptides may self-associate into virus-like particles A gene encoding a Human *enterovirus* A VP2 protein, or immunologically active fragment thereof, may be inserted in a plasmid containing a suitable promoter and expressed in a host cell. The isolated Human *enterovirus* A antigen, for example, an HEV71 VP2 protein, may be isolated and used as the basis of an immunogenic composition for use as a vaccine or for diagnostic use.

A gene encoding a Human *enterovirus* A VP4 protein, or immunologically active fragment thereof, may be inserted in a plasmid containing a suitable promoter and expressed in a host cell. The isolated VP4 protein may be isolated and used as the basis of an immunogenic composition for use as a vaccine or for diagnostic use.

A gene encoding a Human *enterovirus* A VP0 protein, or immunologically active fragment thereof, may be inserted in a plasmid containing a suitable promoter and expressed in a host cell. The isolated VP0 protein may be isolated and used as the basis of an immunogenic composition for use as a vaccine or for diagnostic use.

A gene encoding a Human *enterovirus* A VP0 protein, or immunologically active fragment thereof, may be operably linked to a suitable promoter and inserted into a plasmid, which plasmid exhibits a Human *enterovirus* A protease linked to a suitable promoter to provide a doubly recombinant plasmid, which doubly recombinant plasmid may ultimately be expressed in a eukaryotic or prokaryotic cell expression system.

The Human *enterovirus* A genes and nucleic acids comprised in the expression cassette may be introduced into an appropriate host cell by means known to those skilled in the art. The host cells are propagated and cultured under conditions which allow expression of Human *enterovirus* A genes and proteins.

The invention encompasses a vaccine comprising one or more immunologically active antigens comprising one or more Human *enterovirus* A VP0, VP1, VP2, VP3, VP4 polypeptides, and immunologically active fragments thereof, which vaccine elicits a protective and/or neutralizing immune response directed against a human *Enterovirus*.

The in an embodiment, the expression cassette consists essentially of a nucleic acid encoding a Human *enterovirus* A P1 polyprotein, an IRES and an *enterovirus* 3CD protease under the translational control of the IRES, which protease processes the *enterovirus* P1 polyprotein into *Enterovirus* structural capsid proteins. The structural proteins may take the form of VLPs, capsomers, complexes and/or aggregates.

Indeed, the expression of one or more of the *Enterovirus* proteins as described herein provides antigens which elicit antibodies, which antibodies are functional and able to neutralize enteroviruses selected from HEV71, *coxsackievirus* A16, Human *enterovirus* C or any other picornavirus to high titre.

The expression of one or more of the *Enterovirus* proteins suggests that VP2 and/or VP0 polypeptides contain epitopes recognized by neutralizing antisera.

These functional antibodies surprisingly bind more strongly to *enterovirus* VP2 and VP0 polypeptides than to VP1 polypeptides, which VP1 polypeptide is understood in the art to be the major capsid protein required for the generation of neutralizing antibodies. It is unexpected that VP2 polypeptides are, in fact, important for generating neutralizing antibodies against HEV71 infection.

Thus, it is surprising that an *enterovirus* VP2 polypeptide is the dominant epitope, or antigenic determinant, of the capsid proteins for the generation of neutralizing antibodies against *Enterovirus* infection. HEV71 VP2 polypeptides, either alone, or in combination with other HEV71 capsid proteins, for example VP0 polypeptides, is the dominant antigen which elicits neutralizing antibodies directed against HEV71.

In an aspect of the invention, prophylactic vaccinations for prevention of *Enterovirus* infection are contemplated which vaccines incorporate VP0 and/or VP2 structural proteins of human enteroviruses into an immunogenic composition. The immunogenic composition or vaccine may comprise VP0 or VP2 structural proteins from Human *enterovirus* A, including HEV71 and *coxsackievirus* A16, or a combination thereof. The immunogenic composition may be administered to a subject to elicit neutralizing antibodies directed against human enteroviruses. The immunogenic composition may be comprised in a vaccine which is administered to a subject for the prevention of hand, foot and mouth disease infection caused by Human *enterovirus* A, such as from viruses HEV71 and/or *coxsackievirus* A16.

In another aspect of the invention, therapeutic vaccinations are provided to prevent and/or relieve complications of HEV71 and/or *coxsackievirus* A16 infection, for example, the neurologic and cardiovascular complications manifesting as syndromes such as meningitis, encephalitis, acute flaccid paralysis, pulmonary edema and cardiac failure.

In an aspect of the invention, prophylactic vaccinations for prevention of *Enterovirus* infection are contemplated which vaccines incorporate VP0 or VP2 structural proteins from Human *enterovirus* C, for example PV1, PV2, PV3 structural proteins, or combinations thereof, or biologically or immunologically active fragments thereof. The immunogenic composition may be comprised in a vaccine which is administered to a subject for the prevention of polio caused by Human *enterovirus* C, including PV1, PV2, and PV3.

Furthermore, the immunogenic composition or vaccine may comprise a combination of antigens derived from both Human *enterovirus* C and Human *enterovirus* A.

Reference may now be made to various embodiments of the invention as illustrated in the attached figures. In these embodiments it should be noted that the *enterovirus* VLPs, capsomers, antigens, and aggregates and specific constructs of DNA recombinant molecules are given by way of example.

It may be concluded that *enterovirus* VP2 polypeptides are important to achieve neutralizing antibodies. VP2 polypeptides may be sufficient for formulating a vaccine against an infection with picornaviruses, such as Human *enterovirus* A, types HEV71 and *coxsackievirus* A16; Human *enterovirus* C types 1, 2 and 3: and Human *enterovirus* D type EV68.

In an aspect of the invention, prophylactic vaccinations for prevention of picornavirus infection are contemplated which vaccinations incorporate at least VP0 and/or VP2 and VP4 structural proteins of the virus into an immunogenic composition. The immunogenic composition may be administered to a subject to elicit neutralizing antibodies directed against a picornavirus. The immunogenic composition may be comprised in a vaccine which is administered to a subject for the prevention of picornavirus infection.

In another aspect of the invention, therapeutic vaccinations are provided to prevent and/or relieve complications of picornavirus infection, for example, the neurologic and cardiovascular complications manifesting as syndromes such as meningitis, encephalitis, acute flaccid paralysis, pulmonary edema and cardiac failure.

In a further aspect of the invention there is provided a vaccine composition according to the invention for use in medicine.

In yet another aspect, the invention provides a bivalent, or multivalent vaccine comprising *enterovirus* VP0 and/or VP2 and/or VP4 antigens. For example, Human *enterovirus* A VP0 and/or VP2 and/or VP4 antigens may be combined. Moreover, the aforementioned antigens from different serotypes of Human *enterovirus* A, such as antigens from *coxsackievirus* A16 and HEV71, may be combined in a vaccine, for example, directed against human foot-and-mouth disease.

The *Enterovirus* antigens of bivalent or multivalent vaccines may be produced from the expression cassettes described herein. The *Enterovirus* antigens may be in the form of virus-like particles, capsomers, complexes, and/or aggregates.

In yet another aspect, the invention provides a bivalent, or multivalent vaccine comprising *Enterovirus* antigen(s), and an antigen providing immunity against one or more of the following pathogens: diphtheria (D); tetanus (T); pertussis (P); *Haemophilus influenzae* b (Hib); Hepatitis A (HA) Hepatitis B (HB), and Human *Enterovirus* 71.

In a pediatric vaccine, other compatible antigens may also be included, e.g., antigens known to be effective against meningitis B, meningitis A and C, and otitis media.

The amount of picornavirus antigen in each vaccine dose is selected as an amount which induces an immunoprotective response without significant adverse side effects in typical vaccines. Such amount will vary depending on which specific immunogens are employed. An optimal amount for a particular vaccine can be ascertained by standard studies involving observation of antibody titers and other responses in subjects. A primary vaccination course may include 2 or 3 doses of a vaccine, given at intervals optimal for providing an immunoprotective response.

The invention thus provides a method for preventing picornavirus infections in humans, which method comprises treating a human subject in need thereof with an immunologically effective dose of a vaccine according to any aspect of the invention as hereinabove described.

As used herein and in the claims, the terms and phrases set out below have the meanings which follow.

"Antibody" refers to an immunoglobulin molecule produced by B lymphoid cells with a specific amino acid sequence evoked in humans or other animals by an antigen (immunogen). These molecules are characterized by reacting specifically with the antigen.

"Antibody response" or "humoral response" refers to a type of immune response in which antibodies are produced by B lymphoid cells and are secreted into the blood and/or lymph in response to an antigenic stimulus. In a properly functioning immune response, the antibody binds specifically to antigens on the surface of cells (e.g., a pathogen), marking the cell for destruction by phagocytotic cells and/or complement-mediated mechanisms.

"Antigen" refers to any substance that, as a result of coming in contact with appropriate cells, induces a state of sensitivity and/or immune responsiveness and that reacts in a demonstrable way with antibodies and/or immune cells of the sensitized subject in vivo or in vitro.

"Epitope" refers to the simplest form of an antigenic determinant, on a complex antigen molecule. This is the specific portion of an antigen that is recognized by an immunoglobulin or T-cell receptor.

"Fusion protein" refers to a protein antigen formed by expression of a polypeptide made by combining two or more gene sequences derived from different *Enterovirus* structural proteins.

"Immunologically active fragments" or "biologically active fragments" are fragments of *Enterovirus* structural proteins which elicit neutralizing antibodies directed against enteroviruses. Accordingly, in the context of the invention, such immunologically active fragments are presented to the immune system of an organism in order to affect, or more preferably to induce, a specific immune response and, thereby, vaccinate or prophylactically protect the organism against an infection with an *Enterovirus*.

Neutralizing antibody immune response is where specialized cells of the immune system recognize the presentation of such heterologous proteins, peptides or epitopes and launch a specific immune response.

In an embodiment, the vaccine antigen according to the invention can induce a protective immune response. The term "protective immune response" and/or "neutralizing immune response" as used herein is intended to mean that the vaccinated subject may resist or protect itself against an infection with the pathogenic agent against which the vaccination was done.

"Cellular response" or "cellular host response" refers to a type of immune response mediated by specific helper and killer T-cells capable of directly eliminating virally infected or cancerous cells.

"Antigen-presenting cell" refers to the accessory cells of antigen inductive events that function primarily by handling and presenting antigen to lymphocytes. The interaction of antigen presenting cells (APC) with antigens is an essential step in immune induction because it enables lymphocytes to encounter and recognize antigenic molecules and to become activated. Exemplary APCs include macrophages, Langerhans-dendritic cells, Follicular dendritic cells, and B cells.

"B-cell" refers to a type of lymphocyte that produces immunoglobulins or antibodies that interact with antigens.

"Cytotoxic T-lymphocyte" is a specialized type of lymphocyte capable of destructing foreign cells and host cells infected with the infectious agents which produce viral antigens.

The language "consisting essentially of" means that in addition to those components which are mandatory, other components may also be present in compositions, provided that the essential, basic and/or novel characteristics of the compositions are not materially affected by their presence.

The language "operably linked" means that the components described are in a relationship permitting them to function in their intended manner. Thus, for example, a promoter "operably linked" to a nucleic acid means that the promoter and the nucleic acids of a cistron, or more than one cistron, are combined in such a manner that a single cistronic, a single bicistronic, or a single multicistronic messenger RNA (mRNA) may be produced. Protein expression of the messenger RNA may be regulated according to transcriptional/translational elements of the nucleic acid sequence. An IRES sequence which is inserted into an expression cassette in an orientation which is upstream (5') to a cistron means that the IRES sequence and the nucleic acids of the cistron are ligated in such a manner that translation of the cistronic mRNA is regulated under the control of the IRES.

Reference may now be made to various embodiments of the invention as illustrated in the attached figures. In these embodiments it should be noted that the picornavirus VLPs, capsomers, antigens, and aggregates and specific constructs of DNA recombinant molecules are given by way of example.

Example 1. Description of HEV71 VLP Expression Cassettes and Vectors

Expression cassettes may be constructed through means understood in the art.

1.1 HEV71 VLP Expression Cassette [P1+IRES+3CD]
Features:
Cassette size: 5172 bp
prPs: Pox virus strong early/late synthetic promoter, 43 bp
P1: P1 protein coding sequence from EV71-SB12736-SAR-03 (GenBank Accession: DQ341362) with the addition of a stop codon, 2588 bp
IRES: Internal Ribosome Binding site, 585 bp
3CD: C and D protein coding sequence of P3 from EV71-SB12736-SAR-03 (GenBank Accession: DQ341362) with the addition of a ATG start codon and stop codon, 1940 bp
Pac I: Rare cutters, enables cassette to be cloned into pSNX01 (MVA del 3 integration vector)
The cassette was cloned into pDONR221 Gateway entry vector (Invitrogen) to produce pSN01.
See FIG. 1 for a diagram of the expression cassette and the pSN01 plasmid.

Figure 2:
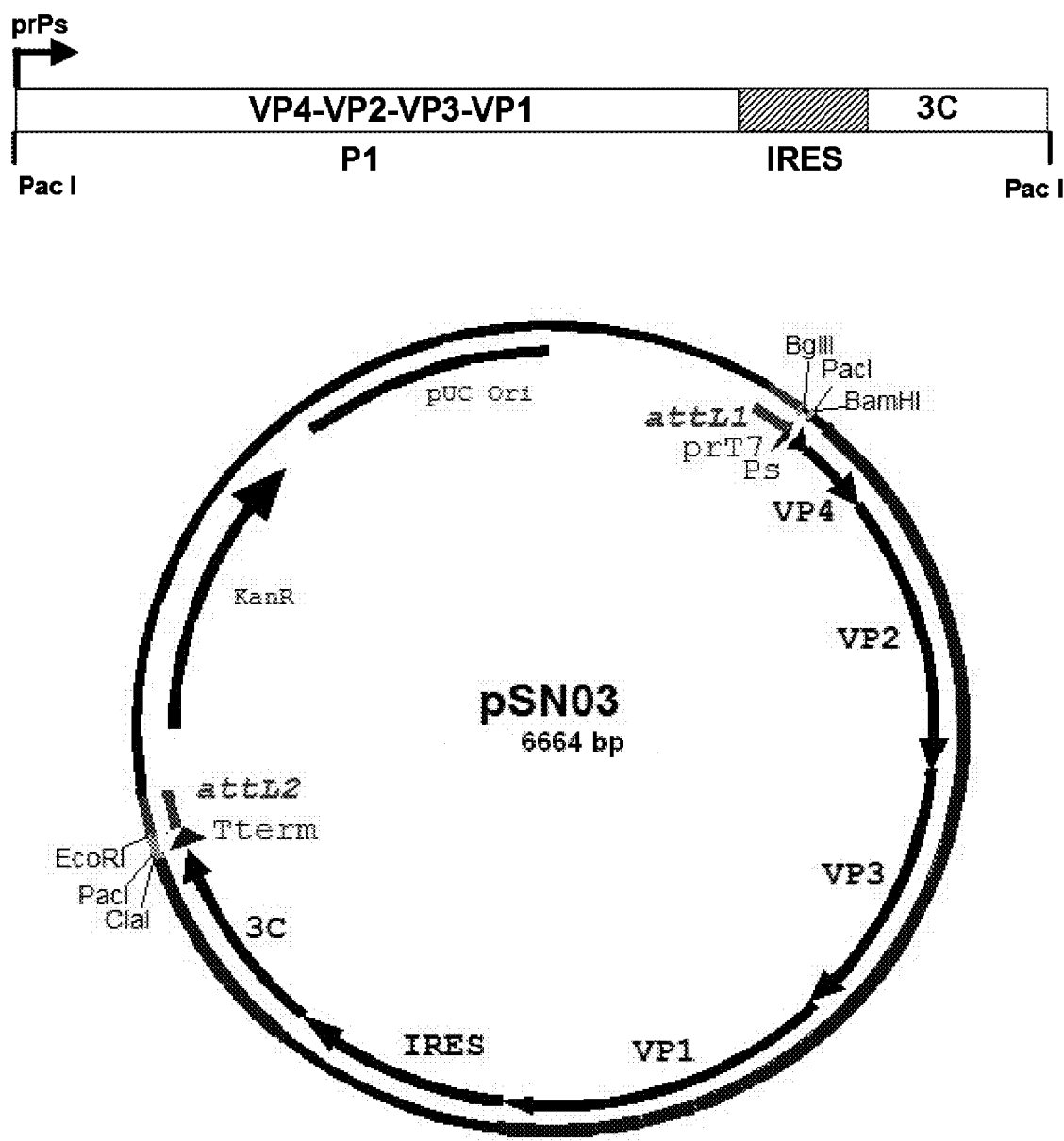
FIG. 2. HEV71 VLP expression cassette [P1+IRES 3C] and the pSN03 plasmid.
Figure 3:
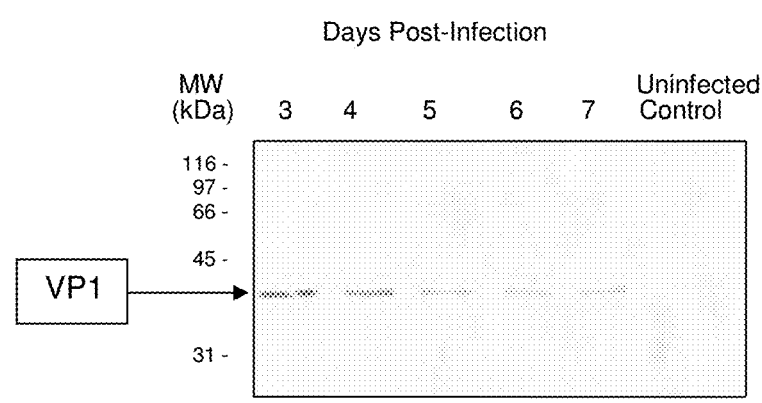
FIG. 3. Expression of VP1 in supernatant of SN07 infected Sf9 cells.
Figure 4:
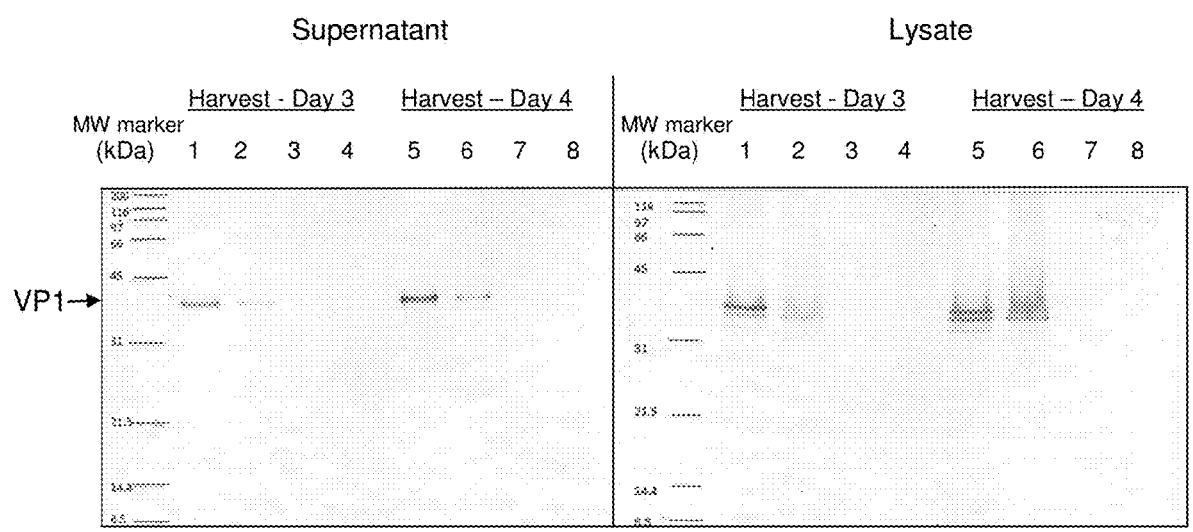
FIG. 4. Processed VP1 in both the supernatants and the lysates.
Figure 5:
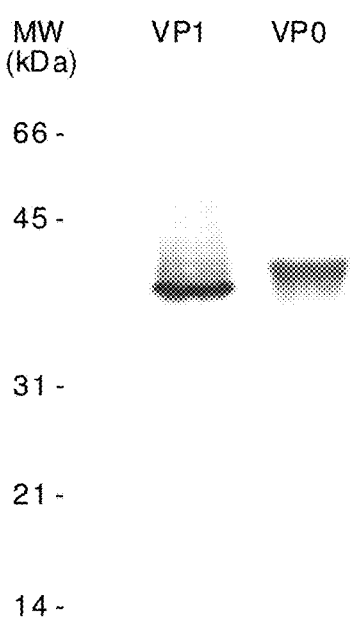
FIG. 5. VP1 and VP0 are in the retentate after ultrafiltration over a 100 kDa molecular weight cut off (MWCO) membrane.
Figure 6:
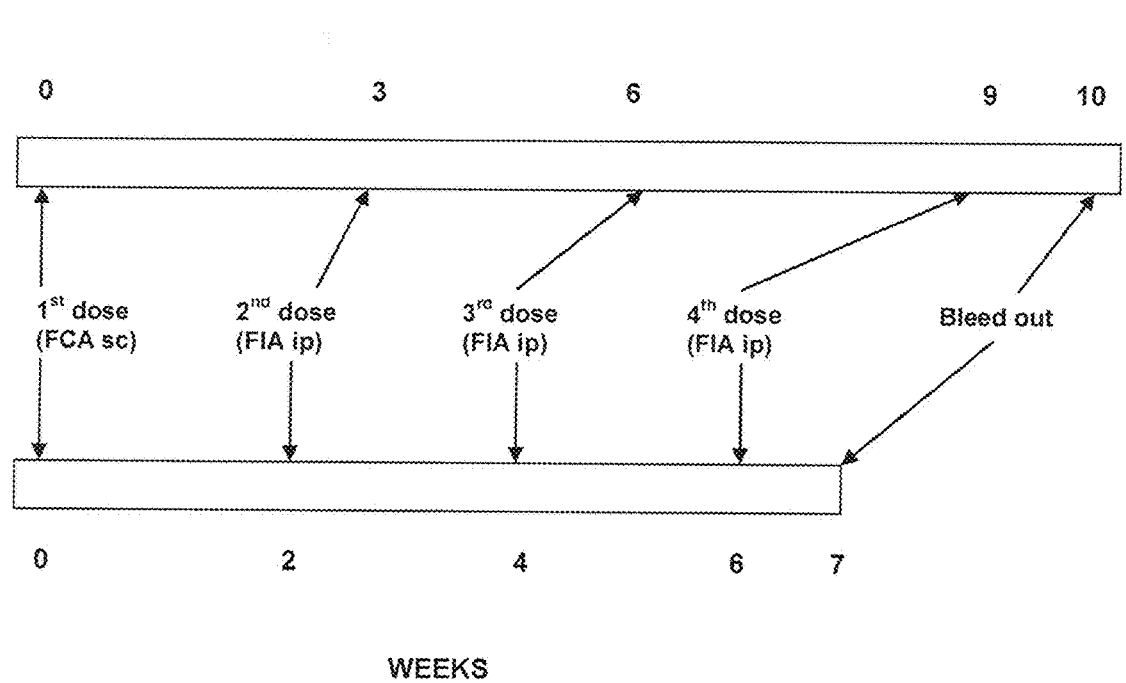
FIG. 6. Immunization schedules to produce neutralizing antibodies. FIRST PROOF OF CONCEPT OF OUR STRATEGY: TWO IMMUNIZATION SCHEDULES (4 mice per group).

1.2 HEV71 VLP Expression Cassette [P1+IRES+3C]
Features:
Cassette size: 3773 bp
prPS: Pox virus strong early/late synthetic promoter, 43 bp
P1: P1 protein coding sequence from EV71-SB12736-SAR-03 (GenBank Accession: DQ341362) with the addition of a stop codon, 2588 bp
IRES: Internal Ribosome Binding site, 585 bp 3CD: C protein coding sequence of P3 from EV71-SB12736-SAR-03 (GenBank Accession: DQ341362) with the addition of a ATG a start codon and stop codon, 551 bp
Pac I: Rare cutters, enables cassette to be cloned into pSNX01 (MVA del 3 integration vector)
The cassette was cloned into pDONR221 Gateway entry vector (Invitrogen) to produce pSN03.
See FIG. 2 for a diagram of the expression cassette and the pSN03 plasmid.

1.3 Methods for Obtaining Recombinant Baculoviruses Containing the Insert HEV71[P1+IRES+3CD] or [P1+IRES+3C]
The source material for HEV71 P1 plus 3CD was pSN01 and for P1 plus 3C was pSN03. The aim was to introduce the HEV71-VLP cassette from pSN01 and pSN03 (Entry vectors) into the baculovirus expression plasmid pDEST8 (Destination vector) by attL/aaR in vitro recombination using LR CLONASE®, following the instructions in the Invitrogen BAC-TO-BAC® manual (2009).

Two recombinase reactions were set up:
1. pSN01 (EV71-P1+3CD)×pDEST8 to produce pSN07;
2. pSN03 (EV71-P1+3C)×pDEST8 to produce pSN08
pSN07 and pSN08 were used to produce recombinant bacmids bacSN07 and bacSN08 by transforming DH10bac as described in the Invitrogen BAC-TO-BAC® manual. The recombinant bacmids were transfected into Sf9 cells to rescue recombinant baculoviruses SN07 and SN08.
The recombinant baculoviruses SN07 and SN08 were used to further infect Sf9 cells in 6 well plates to evaluate for expression of processed capsid proteins. A polyclonal rabbit antiserum specific for VP1 was used to identify VP1 protein in Western blots of lysates and supernatants from recombinant baculovirus infected Sf9 cells.

1.4 Expression of VP1 in the Supernatant of SN07 Infected Sf9 Cells.

Supernatants of infected Sf9 cells were harvested daily from day 3 to day 7 post infection and the proteins were resolved on a 12% SDS-PAGE and transferred to nitrocellulose membranes which were then probed with polyclonal rabbit anti-VP1 antisera (1:4000 dilution) overnight followed by anti-rabbit conjugated with HRP (1:1000 dilution) for 1 hour at room temperature. The Western blots were subsequently developed using TMB. The results are shown in FIG. 3. It was observed that the HEV71 VP1 was processed and that expression of the protein was observed in the supernatant at day 3 and day 4 post infection and that the amount of VP1 expression diminished thereafter. Recombinant baculovirus SN07 on infection of Sf9 cells generates antigens which are found in the supernatant.

Example 2. Processed VP1 in Both the Supernatants and the Lysates

Sf9 cells were infected at a Multiplicity of Infection (MOI) of 10 with different recombinant baculovirus isolates, including SN07, SN08, a control baculovirus bacGUS and mock infected. Supernatants and lysates were harvested on days 3 and 4 post infection and expression of the proteins evaluated by Western blots using rabbit anti-VP1 antisera (1:4000 dilution) to compare yields of proteins produced by SN07 and SN08. As shown in FIG. 4, expression construct SN07 produced more cleaved VP1 than expression construct SN08 both in the supernatant and in the lysate on both days 3 and 4 post infection.

Example 3. VP1 and VP0 is in the Retentate after Ultrafiltration Over a 100 kD Molecular Weight Cut Off (MWCO) Membrane Supernatants from SN07 infected Sf9 cells at day 3 post-infection were clarified and were passed through AMICON® filters (Millipore Corp.) with a 100 kDa MWCO. The retentate was tested for the presence of processed VP1 and VP0. Since the molecular weight of VP1 is approximately 33 kDa, and the molecular weight of VP0 is 36 KDa, these proteins would not be expected to remain in the retentate unless they were in an oligomeric form. As shown in FIG. 5, these antigens remain in the retentate on passing the supernatants through a 100 kDa MWCO ultrafilter. This suggests that the antigens are associated in an oligomeric form. Thus, it may be concluded that VP1 and VP0 are processed and are in an oligomeric association with other capsid proteins.

Example 4. The Retentate, when Used to Immunize Mice, Elicits Strong Neutralizing Antibodies Against HEV71

Two groups of outbred white mice were immunized with the supernatant concentrate from Sf9 infected with SN07 as prepared in Example 3. The immunization schedules used are shown in the diagram in FIG. 6.

All mice in the immunized group produced antibodies that neutralized HEV71 as shown in Table 1. The retentate, when used to immunize mice, elicits strong neutralizing antibodies against HEV71.

TABLE 1

Neutralizing antibodies directed against HEV71.

| mouse ID | neut reciprocal titre |
|---|---|
| m1-1 | 160 |
| m1-2 | 640 |
| m1-3 | >=2560 |
| m1-4 | 640 |
| m2-1 | 80 |
| m2-2 | 640 |
| m2-3 | 640 |
| m2-4 | 160 |
| control1 | <10 |
| control2 | <10 |

Thus, it may be concluded that the oligomeric proteins are able to elicit neutralizing antibodies in mice.

The oligomeric proteins may be utilized in immunogenic compositions and/or comprised in vaccines for administration and prophylaxis of *Enterovirus* infection.

Example 5. VP0 is Expressed in the Lysates of SN07 Infected Sf9 Cells

Sf9 cells were infected with SN07 and the lysates were harvested at 72, 96 and 120 hours. Immunoblots were probed with rabbit polyclonal antisera directed against EV71 VP0 and it was shown that VP0 is expressed at 72 hours post infection. As shown in FIG. 7, the VP0 was partially cleaved to VP2 starting at 96 hours post infection. Thus both VP0 and VP2 are present in the lysates of SN07 infected cells.

Example 6. Pooled Neutralizing Sera from Mice Immunized with the Oligomeric Antigens in the Supernatant of SN07 Infected Sf9 Cells have High Titres Against Recombinant VP2 in ELISA ELISA plates were coated with equal amounts of recombinant VP1 and VP2 and used to test pooled neutralizing mouse antisera. FIG. 8 shows that the mice which received the supernatant retentate antigen preparation were able to bind VP2 better than VP1. Thus, it may be concluded that the antibodies are functional and able to neutralize HEV71 to high titre.

Example 7. Pooled Neutralizing Sera from Mice Immunized with Oligomeric Antigens in the Supernatant of SN07 Infected Sf9 Cells Bind More Strongly to VP2 and VP0 than to VP1

The Western blots in FIG. 9 show that the neutralizing pooled mouse antisera bound more strongly to VP2 and VP0 than to VP1 even though the same amount of total protein was added to each well. This suggests that VP2 and VP0 contain epitopes recognized by neutralizing antisera.

These functional antibodies surprisingly bind more strongly to VP2 and VP0 than to VP1 which is considered to be the major capsid protein required for the generation of neutralizing antibodies. It is thus relevant to consider that VP2 is in fact important for generating neutralizing antibodies.

It may be concluded that the presence of VP2 in a vaccine formulation is important to achieve neutralizing antibodies. VP2 may be sufficient for formulating a vaccine against HEV71 and other species A, B and C enteroviruses including human *coxsackievirus* A16, Echovirus 30, and *Poliovirus* types 1, 2 and 3.

It will further be appreciated that the invention includes within its scope a method of generating an immune response directed against *Poliovirus* including the step of administering an effective amount of a vaccine comprising a *Poliovirus* antigen.

Example 8. Comparison of the Levels of Neutralizing Antibodies

Immunogenic compositions comprising HEV71 VP1 are used to immunize mice. Similarly, immunogenic compositions comprising HEV71 VP2 and/or VP0 are used to immunize mice. The neutralizing antibody levels in the mice immunized with HEV71 VP2 and/or VP0 are compared with the neutralizing antibody levels in the mice immunized with HEV71 VP1. The neutralizing antibody levels in the mice immunized with HEV71 VP2 and/or VP0 are significantly higher than the neutralizing antibody levels in the mice immunized with HEV71 VP1.

Example 9. Construction of Recombinant Baculovirus Vector for Expression of the Human *enterovirus* C P1 Region and the Protease 3CD from a Single Bicistronic Message This example provides a method that will result in the efficient production of VLPs of Human *enterovirus* C (*Poliovirus*) by reducing the protease 3CD mediated killing of baculovirus infected cells.

The construction of a recombinant baculovirus vector for the expression of the P1 region and the protease 3CD from a single bicistronic message is shown, for example, in FIG. 1. The 3CD protease gene is translated in a cap-independent fashion under control of the EMCV IRES. This system provides the leverage to regulate the expression of protease 3CD, i.e., evaluate the mutant IRES sequences to find the weakest IRES so that a lesser amount of protease is produced compared to the P1 proteins.

A bicistronic vector is constructed in which the plasmid contains a polyhedrin promoter upstream of the coding sequence for the P1. Downstream from the cistrons encoding P1 is an Encephalomyocarditis virus (EMCV) internal ribosome entry site (IRES) sequence (GenBank accession number AF113968.2; nucleotides 1666 to 2251) followed by the cistrons containing the nucleotide sequence encoding the protease 3CD. The source material for the Human *enterovirus* C P1 with 3CD may be accessed at the American Type Culture Collection (ATCC) and synthesized from known Human *enterovirus* C sequences (GenBank available through the National Center for Biotechnology Information (NCBI)).

Recombinant baculoviruses are generated using the BAC-TO-BAC® system according to the manufacturer's instructions (Invitrogen). Briefly, LR CLONASE® is used to introduce the Human *enterovirus* C VLP cassette into the baculovirus expression plasmid pDEST8 (Destination using vector) by attL/aaR in vitro recombination. The LR CLONASE® reaction is carried out at 25° C. for 1 hour followed by incubation with proteinase K. The LR CLONASE® reaction mix is transformed into Library Efficiency DH5α competent cells to obtain expression clones. DNA is isolated from the resultant colonies and are confirmed for the presence of the Human *enterovirus* C cassette by restriction enzyme analysis. Recombinant bacmids are constructed by introducing the expression cassette, into the baculovirus genome harbored in DH10bac cells by T7 transposition recombinase. The recombinant bacmids are verified by their white phenotype on LB agar plates supplemented with 50 μg/ml kanamycin, 7 μg/ml gentamicin, 10 μg/ml tetracycline, 100 μg/ml X-gal, and 40 μg/ml IPTG. The PureLink HiPure Plasmid DNA Miniprep Kit (Invitrogen) is used to purify high quality bacmid DNA from DH10Bac *E. coli*. M13 forward, M13 reverse and internal primers from the insert are used to confirm the existence of the Human *enterovirus* C cassette. EFFECTENE® transfection reagent (Qiagen) is used to rescue recombinant baculoviruses by transfecting the DNAs into Sf9 insect cells. Briefly, Sf9 cells are seeded at 2 million per T25 flask and incubated to adhere for 6 hr at 28° C. One microgram of recombinant bacmid DNA is resuspended in 150 μl of DNA condensation buffer and 8 μl of enhancer solution is mixed and incubated at room temperature for 5 minutes. Then 25 μl of EFFECTENE® reagent is added into the DNA mix and incubated for 10 minutes at room temperature. One ml culture medium is added into the tubes containing the transfection complexes and transferred into cell culture flasks and uniformly distributed. At day 3, the supernatant is harvested by centrifugation at 500 g for 5 minutes. Following transfection, a high titer viral stock is prepared. Once a high viral stock is obtained, it is employed to determine the optimal times for target protein expression.

Example 10. Production of VLPs of HEV71, as Well as Human *enterovirus* C, by Means of Reducing the Protease 3CD Mediated Killing of Baculovirus Infected Cells This experiment describes the construction of recombinant baculovirus vector for the expression of the P1 region and the protease 3CD from a single bicistronic message. The protease gene 3CD is translated in a cap-independent fashion under control of the EMCV IRES, shown in FIG. 10. This system provides the leverage to regulate the expression of protease 3CD, i.e., evaluate the mutant IRES sequences to find weakest IRES so that a lesser amount of the protease is produced compared to the P1 proteins.

A bicistronic vector was constructed in which a plasmid contains a polyhedrin promoter upstream of the coding sequence for the P1. Downstream from the cistrons encoding P1 is an Encephalomyocarditis virus (EMCV) internal ribosome entry site (IRES) sequence followed by the cistrons containing nucleotide sequence encoding the protease 3CD, see FIG. 1. The IRES used in Example 1 contains native EMCV IRES sequence as there are altered forms. The native EMCV IRES sequence in FIG. 10 shows the A6 bifurcation loop in the JK segment. Adding one nucleotide, for example an adenine (A7), reduces the expression. Also, in the construct used in Example 1, the 3CD protease is fused with Encephalomyocarditis virus IRES at the amino-terminus. Importantly out framing the EMCV start codon with 3CD protease coding sequence should considerably reduce the expression of downstream genes, see FIG. 11. Both modifications are incorporated into the EMCV IRES sequence of pSN01 and named pSN01-M1, as shown in FIG. 12, and synthesized by DNA2.0.

Experiments were designed to characterize the VLPs expressed from the mutant EMCV IRES of pSN01-M1. Recombinant baculoviruses were generated using the BAC- TO-BAC® system according to the manufacturer's instructions (Invitrogen). Briefly, LR CLONASE® was used to introduce the HEV71 VLP cassette into the baculovirus expression plasmid pDEST8 (Destination using vector) by attL/aaR in vitro recombination. The LR CLONASE® reaction was carried out at 25° C. for 1 hr followed by incubation with proteinase K. The LR CLONASE® reaction mix was transformed into Library Efficiency DH5α competent cells to obtain expression clones. DNA was isolated from the resultant colonies and confirmed for the presence of the HEV71/Poliovirus cassette by restriction enzyme analysis. Recombinant bacmids are constructed by introducing the expression cassette of pSN07-M1, into the baculovirus genome harbored in DH10bac cells by T7 transposition recombinase to give bacSN07-M1. The recombinant bacmids are verified by their white phenotype on LB agar plates supplemented with 50 μg/ml kanamycin, 7 μg/ml gentamicin, 10 μg/ml tetracycline, 100 μg/ml X-gal, and 40 μg/ml IPTG. The PureLink HiPure Plasmid DNA Miniprep Kit (Invitrogen) was used to purify high quality bacmid DNA from DH10Bac *E. coli*. M13 forward, M13 reverse and internal primers from the insert were used to confirm the existence of the HEV71/Poliovirus cassette. EFFECTENE® transfection reagent (Qiagen) was used to rescue recombinant baculoviruses by transfecting the DNAs into Sf9 insect cells. Briefly, Sf9 cells were seeded at 2 million per T25 flask and incubated to adhere for 6 hr at 28° C. One microgram of recombinant bacmid DNA was resuspended in 150 μl of DNA condensation buffer and 8 μl of enhancer solution is mixed and incubated at room temperature for 5 minutes. Then 25 μl of EFFECTENE® reagent was added into DNA mix and incubated for 10 minutes at room temperature. One ml culture medium was added into the tubes containing the transfection complexes and transferred into cell culture flasks and uniformly distributed. At day 3 the supernatant was harvested by centrifugation at 500 g for 5 minutes. Following transfection, a high titer viral stock is prepared. Once a high viral stock is obtained, it is employed to determine the optimal times for target protein expression. For the analysis of the protein of interest, Sf9 cells grown in 10% Grace's insect cell medium (Invitrogen) were resuspended in 1% FBS Sf900-II SFM medium (Invitrogen) to get single cells and were seeded at a million per ml density in the flasks and incubated for 4 hr at 28° C. Viral stocks were added into the PBS washed cells at an MOI of 10 and rocked gently for 1 hr. The infected cells were washed three times with PBS and the cells were grown in Sf900II-SFM for different time points. Cells were lysed with hypotonic douncing buffer/1% TRITON® X-100 (TX-100) (1.5 mM $MgCl_2$, 50 mM KCl, 20 mM HEPES, 1% TX-100) by rocking the flask for 30 minutes at room temperature and cell lysates were prepared by collecting the lysed cells from the flask and centrifuging at 4° C. for 30 minutes at 7000 rpm. The components of the cell lysates and supernatants were analyzed by immunoblotting and ELISA using specific antibodies.

Example 11. Efficient Production of VLPs of HEV71, as Well as Human *enterovirus* C (*Poliovirus*) by Means of Reducing the Protease 3CD Mediated Killing of Baculovirus Infected Cells The construction of a recombinant baculovirus vector for expression of the P1 region and the protease 3CD from a single bicistronic message is shown in FIG. 1. The 3CD protease gene is translated in a cap-independent fashion under control of the EMCV IRES, shown in FIG. 10. This system provides the leverage to regulate the expression of 3CD protease, i.e., evaluate the mutant IRES sequences to find the weakest IRES so that a lesser amount of protease is produced compared to the P1 proteins.

A bicistronic vector was constructed and the plasmid contains a polyhedrin promoter upstream of the coding sequence for the P1. Downstream from the cistrons encoding P1 is an Encephalomyocarditis virus (EMCV) internal ribosome entry site (IRES) sequence followed by the cistrons containing a nucleotide sequence encoding the 3CD protease, see FIG. 1. The IRES used in Example 1 contains native EMCV IRES sequence as there are altered forms. The native EMCV IRES sequence has the A6 bifurcation loop in the JK segment, indeed by adding one nucleotide (A7) known to reduce the expression, see FIG. 10. The A6 bifurcation loop was modified into A7 in the EMCV IRES sequence of pSN01 and named pSN01-M2, see FIG. 13, which is synthesized by DNA2.0.

VLPs expressed by the mutant EMCV IRES of pSN01-M2 were characterized. Recombinant baculoviruses were generated using the BAC-TO-BAC® system according to the manufacturer's instructions (Invitrogen). Briefly, LR CLONASE® was used to introduce the HEV71 VLP cassette into the baculovirus expression plasmid pDEST8 (Destination using vector) by attL/aaR in vitro recombination. The LR CLONASE® reaction was carried out at 25° C. for 1 hr followed by incubation with proteinase K. The LR CLONASE® reaction mix was transformed into Library Efficiency DH5α competent cells to obtain expression clones. DNA was isolated from the resultant colonies and confirmed for the presence of the HEV71/Poliovirus cassette by restriction enzyme analysis. Recombinant bacmids were constructed by introducing the expression cassette of pSN07-M2, into the baculovirus genome harbored in DH10bac cells by T7 transposition recombinase to give bacSN07-M2. The recombinant bacmids were verified by their white phenotype on LB agar plates supplemented with 50 μg/ml kanamycin, 7 μg/ml gentamicin, 10 μg/ml tetracycline, 100 μg/ml X-gal, and 40 μg/ml IPTG. The PureLink HiPure Plasmid DNA Miniprep Kit (Invitrogen) was used to purify high quality bacmid DNA from DH10Bac *E. coli*. M13 forward, M13 reverse and internal primers from the insert were used to confirm the existence of the HEV71/ *Poliovirus* cassette. EFFECTENE® transfection reagent (Qiagen) was used to rescue recombinant baculoviruses by transfecting the DNAs into Sf9 insect cells. Briefly, Sf9 cells were seeded at 2 million per T25 flask and incubated to adhere for 6 hr at 28° C. One microgram of recombinant bacmid DNA was resuspended in 150 μl of DNA condensation buffer and 8 μl of enhancer solution is mixed and incubated at room temperature for 5 minutes. Then 25 μl of EFFECTENE® reagent was added into the DNA mix and incubated for 10 minutes at room temperature. One ml culture medium was added into the tubes containing the transfection complexes and transferred into cell culture flasks and uniformly distributed. At day 3, the supernatant was harvested by centrifugation at 500 g for 5 minutes. Following transfection, a high titer viral stock was prepared. Once a high viral stock was obtained, it was employed to determine the optimal times for target protein expression. For the analysis of the protein of interest, Sf9 cells grown in 10% Grace's insect cell medium (Invitrogen) were resuspended in 1% FBS Sf900-II SFM medium (Invitrogen) to get single cells and were seeded at a million per ml density in the flasks and incubated for 4 hr at 28° C. Viral stocks were added into the PBS washed cells at an MOI of 10 and rocked gently for 1 hr. The infected cells were washed three times with PBS and cells were grown in Sf900II-SFM for different time points. Cells were lysed with hypotonic douncing buffer/1% TX-100 (1.5 mM $MgCl_2$, 50 mM KCl, 20 mM HEPES, 1% TX-100) by rocking the flask for 30 minutes at room temperature and the cell lysates were prepared by collecting the lysed cells from the flask and centrifuging at 4° C. for 30 minutes at 7000 rpm. The components of the cell lysates and supernatants were analyzed by immunoblotting and ELISA using specific antibodies.

Example 12. Efficient Production of VLPs of HEV71 as Well as Human *enterovirus* C (*Poliovirus*) by Means of Reducing the Protease 3CD Mediated Killing of Baculovirus Infected Cells The construction of a recombinant baculovirus vector for expression of the P1 region and the protease 3CD from a single bicistronic message is shown in FIG. 1. The 3CD protease gene is translated in a cap-independent fashion under control of the EMCV IRES, shown in FIG. 10. This system provides the leverage to regulate the expression of protease 3CD, i.e., evaluate the mutant IRES sequences to find the weakest IRES so that a lesser amount of protease is produced compared to the P1 proteins.

A bicistronic vector was constructed in which the plasmid contains a polyhedrin promoter upstream of the coding sequence for the P1. Downstream from the cistrons encoding P1 is an Encephalomyocarditis virus (EMCV) internal ribosome entry site (IRES) sequence followed by the cistrons containing a nucleotide sequence encoding the protease 3CD (FIG. 1). The IRES used in Example 1 contains native EMCV IRES sequence as there are altered forms. In the pSN01 construct the 3CD protease is fused with Encephalomyocarditis virus polyprotein at the amino-terminus. Out framing the EMCV start codon with 3CD protease coding sequence should considerably reduce the expression of downstream genes, see FIG. 11. This modification was incorporated into EMCV IRES sequence of pSN01 and named pSN01-M3, see FIG. 14, and is synthesized by DNA2.0.

The VLPs expressed by the mutant EMCV IRES of pSN01-M3 were analyzed. Recombinant baculoviruses were generated using the BAC-TO-BAC® system according to the manufacturer's instructions (Invitrogen). Briefly, LR CLONASE® was used to introduce the HEV71 VLP cassette into the baculovirus expression plasmid pDEST8 (Destination using vector), by attL/aaR in vitro recombination. The LR CLONASE® reaction was carried out at 25° C. for 1 hr followed by incubation with proteinase K. The LR CLONASE® reaction mix was transformed into Library Efficiency DH5α competent cells to obtain expression clones. DNA was isolated from the resultant colonies and confirmed for the presence of HEV71/*Poliovirus* cassette by restriction enzyme analysis. Recombinant bacmids were constructed by introducing the expression cassette of pSN07-M3, into the baculovirus genome harbored in DH10bac cells by T7 transposition recombinase to give bacSN07-M3. The recombinant bacmids were verified by their white phenotype on LB agar plates supplemented with 50 μg/ml kanamycin, 7 μg/ml gentamicin, 10 μg/ml tetracycline, 100 μg/ml X-gal, and 40 μg/ml IPTG. The PureLink HiPure Plasmid DNA Miniprep Kit (Invitrogen) was used to purify high quality bacmid DNA from DH10Bac *E. coli*. M13 forward, M13 reverse and internal primers from the insert were used to confirm the existence of the HEV71/*Poliovirus* cassette. EFFECTENE® transfection reagent (Qiagen) was used to rescue recombinant baculoviruses by transfecting the DNAs into Sf9 insect cells. Briefly, Sf9 cells were seeded at 2 million per T25 flask and incubated to adhere for 6 hr at 28° C. One microgram of recombinant bacmid DNA was resuspended in 150 μl of DNA condensation buffer and 8 μl of enhancer solution is mixed and incubated at room temperature for 5 minutes. Then 25 μl of EFFECTENE® reagent was added into the DNA mix and incubated for 10 minutes at room temperature. One ml culture medium was added into the tubes containing the transfection complexes and transferred into cell culture flasks and uniformly distributed. After day 3, supernatant was harvested by centrifugation at 500 g for 5 minutes. Following transfection, a high titer viral stock is prepared. Once a high viral stock is obtained, it is employed to determine the optimal times for target protein expression.

For the analysis of the protein of interest, Sf9 cells grown in 10% Grace's insect cell medium (Invitrogen) were resuspended in 1% FBS Sf900-II SFM medium (Invitrogen) to get single cells and were seeded at a million per ml density in the flasks and incubated for 4 hr at 28° C. Viral stocks were added into the PBS washed cells at a MOI of 10 and rocked gently for 1 hr. The infected cells were washed three times with PBS and cells were grown in Sf900II-SFM for different time points. Cells were lysed with hypotonic douncing buffer/1% TX-100 (1.5 mM $MgCl_2$, 50 mM KCl, 20 mM HEPES, 1% TX-100) by rocking the flask for 30 minutes at room temperature and cell lysates were prepared by collecting the lysed cells from the flask and centrifuging at 4° C. for 30 minutes at 7000 rpm. The components of the cell lysates and supernatants were analyzed by immunoblotting and ELISA using specific antibodies.

Example 13. Mutant IRES Construct M2 Expresses Higher Levels of VP1 in the Supernatant Recombinant baculoviruses expressing HEV71 capsid proteins under the control of the wild type or mutant EMCV IRES's were evaluated with respect to the level of expression of the HEV71 capsid proteins from the ECMV IRES's. Baculovirus produced VLPs which are expressed under the control of the wild type EMCV IRES from SN07 of Example 1, and the 3 mutant IRES's, M1, M2 and M3 from Examples 10, 11, and 12, respectively, were analyzed with respect to the level of baculovirus expression of the HEV71 capsid proteins. A recombinant baculovirus expressing P1 and 3CD under different promoters (F) and a control recombinant baculovirus expressing bacGUS (G) were also included in the study. Sf9 cells were infected at an MOI of 5 and both lysates and supernatants were harvested on day 3 as described in Examples 10-12 above. The lysates and supernatants were probed with an anti-VP1 antibody to detect the expression of HEV71 capsid proteins.

The immunoblots of FIG. 15 show that when lysates were probed with antibodies to VP1, the mutants M1 and M2 express higher levels of VP1 than the mutant M3 or the construct driven by 2 promoters. However, the mutant M2 produced more VP1 in the supernatant. These data are shown in the top panel.

The bottom panel of FIG. 15 shows the blots which were probed with a control anti-gp64 antibody which is directed to the coat protein of baculovirus. The immunoblot shows that equivalent amounts of baculovirus were produced in each sample.

Example 14. Cloning, Expression and Purification of Subunit Vaccines Using a Baculovirus Expression System The present invention is intended for the generation and use of recombinant HEV71 and *Poliovirus* structural proteins which are fused as single immunogens to elicit a protective immune response in vaccinated individuals. The present invention relates generally to preparing recombinant HEV71 and/or *Poliovirus* fusion protein vaccine compositions comprising HEV71 and/or *Poliovirus* subunit protein, or an immunogenic fragment thereof, and an adjuvant in combination with the recombinant HEV71 and/or *Poliovirus* subunit fusion protein. HEV71 and *Poliovirus* subunit fusion proteins may comprise capsid proteins selected from VP1, VP2, VP3, and VP4, combinations thereof, and combinations of immunogenic fragments thereof. In one aspect of this embodiment, the recombinant HEV71 and/or *Poliovirus* fusion protein comprises HEV71 or *Poliovirus* subunit protein and a fusion partner protein in genetic association with the HEV71 or *Poliovirus* subunit protein. The present invention contemplates methods to generate the constructs to express the following subunit vaccines in *E. coli* as well as baculovirus: VP0, VP4-VP2-VP3 fusion, VP2-VP3-VP1 fusion.

To generate cDNAs from HEV71 and/or *Poliovirus* encoding VP0, VP4-VP2-VP3 fusion, or VP2-VP3-VP1, reverse transcription/polymerase chain reaction (The High Pure Nucleic Acid Kit; Roche) was carried out using purified genomic viral RNA. A forward and a reverse primer was made from the 5' and 3' end of the genes and which primers incorporate a start and stop codon. The amplified PCR products were digested with EcoRI and NotI restriction enzymes and cloned into the pFastBac HT vector (Invitrogen) as shown in FIG. 16. The BAC-TO-BAC® expression system from Invitrogen is commercially available and methods were used according to the manufacturer's instructions. The fusion genes are cloned into pFastBac HT donor plasmid and the production of recombinant proteins was based upon the BAC-TO-BAC® to baculovirus expression system (Invitrogen). The pFastBac HT donor plasmid carrying the fusion genes was transferred into a baculovirus shuttle vector (bacmid) by site-specific recombination by T7 transposition recombinase. This was accomplished in *E. coli* strain DH10Bac. The DH10Bac cells contain the bacmid, which conferred kanamycin resistance and a helper plasmid, which encoded the transposase and conferred resistance to tetracycline. The recombinant pFastBac HT plasmids with the gene of interest were transformed into DH10Bac cells for the transposition to generate recombinant bacmids. The transformed cells were serially diluted and each dilution was plated on LB agar plates supplemented with 50 µg/ml kanamycin, 7 µg/ml gentamicin, 10 µg/ml tetracycline, 100 µg/ml X-gal, and 40 µg/ml IPTG and incubated for at least 48 hours at 37° C. The white colonies were picked and re-streaked to confirm a white phenotype. Recombinant bacmids were isolated by the PureLink HiPure Plasmid DNA Miniprep Kit (Invitrogen) and the DNA samples were dissolved in 40 µl of TE (10 mM Tris-HCl pH 8, 1 mM EDTA) and used for transfections.

The isolated bacmid DNA was screened for the inserted gene of interest by PCR. EFFECTENE® transfection reagent (Qiagen) was used to rescue recombinant baculoviruses by transfecting the DNAs into Sf9 insect cells. Briefly, Sf9 cells were seeded at 2 million per T25 flask and incubated to adhere for 6 hr at 28° C. One microgram of recombinant bacmid DNA was resuspended in 150 µl of DNA condensation buffer and 8 µl of enhancer solution is mixed and incubated at room temperature for 5 minutes. Then 25 µl of EFFECTENE® reagent was added into DNA mix and incubated for 10 minutes at room temperature. One ml culture medium was added into the tubes containing the transfection complexes and transferred into cell culture flasks and uniformly distributed. At day 3, the supernatant was harvested by centrifugation at 500 g for 5 minutes. Following transfection, a high titer viral stock is prepared. Once a high viral stock is obtained, it is employed to determine the optimal times for target protein expression. For the analysis of the protein of interest, Sf9 cells grown in 10% Grace's insect cell medium (Invitrogen) was resuspended in 1% FBS Sf900-II SFM medium (Invitrogen) to get single cells and are seeded at a million per ml density in the flasks and incubated for 4 hr at 28° C. Viral stocks were added into PBS washed cells at a MOI of 10 and rocked gently for 1 hr. The infected cells were washed three times with PBS and cells are grown in Sf900II-SFM for different time points. Cells were lysed with hypotonic douncing buffer/1% TX-100 (1.5 mM $MgCl_2$, 50 mM KCl, 20 mM HEPES, 1% TX-100) by rocking the flask for 30 minutes at room temperature and the cell lysates were prepared by collecting the lysed cells from the flask and centrifuging at 4° C. for 30 minutes at 7000 rpm. The expression of the heterologous protein in the cells was verified by SDS polyacrylamide gel electrophoresis (SDS-PAGE) and Western blots using the His Probe-HRP antibody (Thermo Scientific) as the probe. Once production of baculovirus and the expression of protein were confirmed, the virus stock was amplified to produce a concentrated stock of the baculovirus that carry the gene of interest. The most appropriate concentration of the virus to infect insect cells and the optimum time point for the production of the desired protein was also established. For purification under denaturing conditions, the cells were lysed in a lysis buffer containing 6 M guanidinium-HCl in 100 mM $NaH_2PO_4$, 10 mM Tris, 300 mM NaCl, 10 mM imidazole, pH 8.0 (lysis buffer). The suspension was sonicated on ice with 5 pulses of 1 minute per pulse at a power setting of 60 watts, and was mixed at room temperature for 1 hour. The lysate was centrifuged at 27K g for 30 min to eliminate cell debris. The supernatant was loaded on to a HisTrap (GE healthcare life sciences) column pre-equilibrated with lysis buffer. Following loading, the column was washed with 20 column volumes of 6 M guanidinium-HCl in 100 mM $NaH_2PO_4$, 10 mM Tris, 300 mM NaCl, 40 mM Imidazole, pH 8.0 (wash buffer 1), followed by washes with 20 column volumes of 8 M urea in 100 mM $NaH_2PO_4$, 10 mM Tris, 300 mM NaCl, 40 mM imidazole, pH 8.0 (wash buffer 2). The bound protein was eluted with a buffer containing 8 M urea, 100 mM $NaH_2PO_4$, 10 mM Tris, 300 mM NaCl, 250 mM imidazole, pH 8 (Elution Buffer). The fractions containing the protein were pooled and dialyzed against PBS, overnight at 4° C. TEV protease was used for removal of the histidine tag following protein purification according to manufacturer's instructions.

Example 15. Expression and Purification of Human *enterovirus* A and Human *enterovirus* C (*Poliovirus*) Subunit Vaccines in *E. coli*

The Champion™ pET SUMO Expression System (Invitrogen) produces the highest levels of soluble protein in *E. coli*. It utilizes a small ubiquitin-related modifier (SUMO) fusion to enhance the solubility of expressed fusion proteins. After expression, the 11 kD SUMO moiety can be cleaved by the highly specific and active SUMO (ULP-1) protease at the carboxyl terminal, producing a native protein. Also it contains N-terminal 6xHis tag for protein detection and purification.

The construction of pET SUMO-VP0, pET SUMO-VP4-VP2-VP3 and pET SUMO-VP2-VP3-VP1 expression vector for antigenic fusion proteins of HEV71 and *Poliovirus*, as shown in FIG. 17, is as follows. The fragments of VP0, VP4-VP2-VP3 fusion and VP2-VP3-VP1 fusion were used as the antigens for HEV71 and *Poliovirus* subunit vaccines. A SUMO motif and the 6xHistag were conjugated to the N-terminus of fusions to aid in solubilization of the protein and purification of the protein, respectively. The antigenic fusion proteins were created by a gene cloning technology comprising cloning cDNA sequences encoding respective proteins into an expression vector to form expression vectors of pET SUMO-VP0, pET SUMO-VP0, pET SUMO-VP4-VP2-VP3 and pET SUMO-VP2-VP3-VP1. The DNA fragments encoding fusion partners were PCR amplified using specific primers which consist of a start codon and a stop codon in the forward and reverse primers, respectively. Ligation of the PCR product was carried out as follows: fresh PCR product, 10x ligation buffer, pET SUMO vector (25 ng/μl) 2 μl, sterile water added to a total volume of 9 μl, and 1 μl T4 DNA ligase (4.0 Weiss units) was added and the ligation reaction incubated at 15° C. for overnight then proceeded to transforming One Shot® Mach1™-T1R (Invitrogen) competent cells. Ten (10) colonies were selected and plasmid DNA isolated from them using the PureLink™ HQ Mini Plasmid Purification Kit (Invitrogen). The plasmids were analyzed by restriction analysis to confirm the presence and the correct orientation of the insert. From the recombinants, plasmid DNA was isolated as earlier and the plasmids were transformed into BL21 (DE3) One Shot® cells (Invitrogen). The transformants were grown and induction of expression with IPTG at several time points was carried out to determine the optimal time of expression. For each time point, 500 μl was removed from the induced and uninduced cultures and each cell pellet was resuspended in 80 μl of SDS-PAGE sample buffer. After centrifuging the boiled samples, 10 μl of each sample was loaded onto an SDS-PAGE gel and electrophoresed.

To scale-up the purification of recombinant fusion protein using a HisTrap nickel column (GE Healthcare Life Sciences), the following procedure was adapted. An overnight culture (5%) was inoculated into 100-300 ml LB plus 50 μg/ml kanamycin and induced after 2 hrs with 1 mM IPTG. After 2 hrs the cells were harvested by centrifuging at 3000 g for 10 minutes. The pellet was resuspended in 10% (total volume of the culture) the binding buffer (20 mM sodium phosphate, 0.5M NaCl and 20 mM imidazole at pH7.4). The cells were sonicated with Misonic UltraSonicate Liquid processor for five times for a minute with a minute gap in an ice bucket. The sonicated samples were separated into soluble and insoluble form by centrifuging at 4000 rpm for 1 hr at 4° C. The insoluble fraction was resuspended with binding buffer containing 6M urea. Both the soluble and insoluble fractions were centrifuged at 4000 rpm for 1 hr at 4° C. then filtered through 0.22 μm filter unit. A HisTrap column was equilibrated with the binding buffer and filtered samples were loaded onto the column. Next, the column was washed with binding buffer with 40 mM imidazole and the recombinant protein was eluted with binding buffer containing 0.5M imidazole (6M urea for insoluble fraction). All the collected samples were tested using Coomassie blue staining protocol for proteins. Pure recombinant protein containing eluted fraction were dialysed using Merck tubing in Tris-HCl buffer. After the dialysis protein concentrations were estimated using a Bradford reagent. The native protein was generated by using SUMO protease to cleave the N-terminal peptide containing the 6xHis tag and SUMO according to manufacturer's instructions.

Example 16. Antibodies from Pooled Neutralizing Sera from Mice Immunized with SN07 Retentate Binds to all the Components of EV71VLPs The coding sequences of VP1, VP2 and VP0 were separately cloned into the pET SUMO vector as described in Example 15. The individual capsid proteins were expressed in *E. coli* and purified as described in Example 15. The purified proteins VP0, VP1, VP2 and VP3 were subjected to Western blotting and probed with pooled neutralizing sera used in Example 4 at the dilution of 1:1000. Control mice sera used in Example 4 is also included in the studies.

Western blotting results in FIG. 18 show that pooled neutralizing sera from mice immunized with oliogomeric antigens in the supernatant of SN07 infected Sf9 cells bind to all of the VLP components, VP0, VP1, VP2 and VP3.

Example 17. Characterization of HEV71 VLPs—Pull-Down of HEV71 VLPs from Culture Supernatants 20 ml of supernatant from cells infected with recombinant baculovirus SN07 was mixed with 10 ml neutralizing monoclonal antibody (EV18/4/D6-1/F1/G9) and left at room temperature for 1 hr. The mixture was loaded slowly through a 1 ml column of MabSelect SuRe™ (GE Health Care) recombinant Protein A, 85 um agarose bead size, which was pre-equilibrated with PBS, then washed with 20 mls PBS and then eluted with 0.5 ml of 0.1 M glycine-HCl, pH3.0. Fractions were neutralized with 30 μl of Tris-HCl, pH8.8. Elution fractions were run on SDS-PAGE followed by Coomassie blue staining and destaining.

FIG. 19 shows that all of the VLP components (VP0, VP1 and VP3) are visible in the Coomassie blue stained SDS-PAGE gel.

Example 18. Analysis of Affinity Column (AFC) Purified HEV71VLPs

An affinity column (AFC) was prepared with a neutralizing monoclonal antibody (EV18/4/D6-1/F1/G9), which was developed using a baculovirus SN07 supernatant retentate. The eluted fraction was analyzed by Western blotting and is shown in FIG. 20. The eluted fraction in Lanes 1 and 2, probed using an anti-VP1 antibody, shows that VP1 is present in the AFC purified VLPs. The eluted fraction in Lanes 3 and 4, probed using an anti-VP2 antibody, shows that VP2 is also present in the AFC purified VLPs. The eluted fraction in Lanes 5 and 6, probed using an anti-VP2 monoclonal antibody, shows that VP2 is present in the AFC purified VLPs.

Example 19. Electron Micrograph of AFC Purified HEV71 VLPs

The fraction eluted from the affinity column (AFC) of Example 18 was evaluated by electron microscopy. An electron micrograph picture of AFC purified VLPs is shown in FIG. 21. The results of the electron microscopy confirm that HEV71 structural proteins are assembled into VLPs.

Example 20. Mice Protection Studies Using Retentate

Antigen used was a 20x concentrated crude retentate of recombinant baculovirus SN07 prepared as described above. Vaginal plugs indicative of pregnancy was determined the morning after mating, designated as Embryonic Day E0.5. Two doses of 100 μL of retentate mixed with IMJECT® (alum) given i.p. to pregnant dams at E3.5 and, on confirmation of pregnancy by weight measurement, a second dose was given on E17.5. Initial blood sample was collected from each mouse prior to the administration of the first vaccine dose, samples were collected weekly thereafter until 14 days after viral challenge of pups. Three groups of Balb/c mice 20 mice were immunized and then challenged (20 mice), 20 mice were mock-immunised and challenged (20 mice), 5 mice non-immunised, non-challenged Five-day-old pups were infected with 50 µl of MP-26M virus containing 100×HD$_{50}$ of MP-26M. All infected animals were observed twice daily for clinical signs of illness until 14 days post-inoculation. Abnomal signs included failure to thrive; weight loss; runting; stomach empty of milk; lethargy; head tilt; hunched posture; ruffled fur; dehydration, hypothermia; limb paralysis. Paralysis was scored according to the following grading system:

0—normal
1—limb weakness but can still move limbs
2—inability to move affected limbs
3—quadriplegia i.e. inability to move limbs Animals suffering grade 3 paralysis were euthanased by cervical dislocation under anaesthetic (HD$_{50}$). Histopathology was performed on sections from a variety of target organs.

The results of the protection study are shown in Table 2 below.

TABLE 2

83% PROTECTION IN PASSIVE PROTECTION

| VACCINE | NUMBER OF MATED MICE | NUMBER OF PREGNANT MICE | NUMBER OF PUBS/ LITTER | TOTAL NUMBER OF PUBS | NUMBER OF SURVIVED PUBS | SURVIVAL RATE | MEDIAN SURVIVAL (DAYS) |
|---|---|---|---|---|---|---|---|
| RETENTATE | 20 | 2 | 1, 5 | 6 | 5* | 83% | 14 |
| ALUM/PBS | 20 | 2 | 5, 7 | 12 | 0 | 0% | 5 |
| NO VACCINE/ NO CHALLENGE | 5 + 5 | 2 + 1 | 5, 7, 6 | 18 | 18 | 100% | 14 |

Two litters of mice were born to VLP vaccinated mothers. One mother had 5 pups and showed good maternal care. The second mother had one pup that was very weak and did not show good maternal care.

It may be concluded that 83% of mice born to immunized mothers were protected from virus challenge.

A summary of the histopathological observations is shown in Table 3.

TCID$_{50}$ of MP-26M. 83% of mice born to immunized mothers were protected from challenge.

The histopathology results showed that 3 mice from mothers in the HEV71-VLP immunized group which were then challenged with HEV71 virus showed no clinical signs of infection.

However, 3 mice from mothers in the mock-immunized (Alum/PBS) and which were then challenged with HEV71 virus succumbed to infection. Two mice from mothers in the non-immunized, non-challenged group showed no clinical signs of infection.

The VLP vaccine protected one litter of infant mice (5/6 pups from immunized mothers vs 0/12 pups from mock-immunized mothers) against lethal challenge with a B3 genotype mouse-adapted strain of HEV71.

Example 21. Human *enterovirus* C (*poliovirus*-PV) VLP Expression

Variations on *Poliovirus* expression cassettes were constructed to generate *poliovirus* VLPs. The expression cassettes all comprised a *poliovirus* P1 polypeptide and differed with respect to the IRES, which IRES directs the expression of a *Poliovirus* 3CD protease: (PV-P1+HEV71-IRES+PV-3CD); (PV-P1+EMCV-IRES+PV-3CD); (PV-P1+PV-IRES+PV-3CD). Recombinant baculoviruses harboring the *poliovirus* VLP expression cassettes were tested. Lysates from the baculovirus infected cells were harvested on day 3 post

TABLE 3

SUMMARY OF HISTOPATHOLOGICAL OBSERVATIONS
(N = no abnormalities detected)

| VACCINE | AGE | DAYS P1 | MOUSE | SYMPTOMS | SPLEEN | LIVER | HEART | SKELETAL MUSCLE | SPINAL CORD | BRAIN |
|---|---|---|---|---|---|---|---|---|---|---|
| VLP | 19 | 14 | V87P4 | NO CLINICAL SIGNS OF INFECTION | N | N (1) | N | 0.5 | N | N |
|  | 19 | 14 | V87P5 | NO CLINICAL SIGNS OF INFECTION | N | N (1) | N | 0.5 | N | N |
|  | 19 | 14 | V87P6 | NO CLINICAL SIGNS OF INFECTION | N | N (1) | N | N | N | N |
| ALUM/PBS | 10 | 5 | DC4 | GRADE3 PARALYSIS | N | N (2) | N | 3 | N | N |
|  |  |  | DC5 | GRADE3 PARALYSIS | N | N (2) | N | 3 | N | N |
|  |  |  | DC6 | GRADE3 PARALYSIS | N | N (2) | N | 03 | N | N |
| NO VACCINE | 19 | NI | V116P4 | NO CLINICAL SIGNS OF INFECTION | N | N (0.5) | N | N | N | N |
|  |  |  | V116P5 | NO CLINICAL SIGNS OF INFECTION | N | N (0.5) | N | N | N | N |

Five mice gave birth to litters and were included in the vaccine protection study (11% pregnancy rate). The value of the humane endpoint (HD$_{50}$), as calculated by the method of Reed and Muench, 1938, was determined to be $2.0 \times 10^2$ infection and expression of the *poliovirus* VP3 was evaluated using rabbit anti-PVP3 antibodies (1:2000).

Only the PV-IRES-containing construct produced a VP-3 protein of the expected size. Unlike in the PV-IRES construct, the *poliovirus* VP3 protein is not processed properly when the 3CD protease is under the control of HEV71-IRES or EMCV-RES and, consequently, adversely affects the production of *poliovirus* VLPs. Thus, the *poliovirus* PV-VLP expression cassette harboring the PV-IRES is very efficient for *poliovirus* VLP production.

Example 22. ELISA to Demonstrate *poliovirus* PV-VLP Assembly

To demonstrate *poliovirus* VLP generation from the PV-VLP expression cassette, a two sites ELISA was performed using lysates and supernatants from recombinant baculoviruses carrying a PV-VLP expression cassette wherein the PV-3CD protease is under the control of a *poliovirus* IRES. Sf9 cells were infected with the recombinant baculoviruses carrying a PV-VLP expression cassette including PV-IRES. Lysates and supernatants were harvested on day 3 post infection. Formation of the *poliovirus* VLPs was evaluated using a two sites ELISA.

The two sites ELISA procedure was conducted by preparing protein A-purified rabbit anti-*poliovirus* VP3 antibodies as capture antibodies and diluting in coating buffer, 0.05M Carbonate-bicarbonate buffer, pH 9.6, to 50 µg/mL. 100 µl/well of the antibodies was dispensed into NUNC immunoplates and stored at 4° C. overnight. After washing with PBST (0.05%), the immunoplates were blocked with 200 µl/well blocking buffer, 1% casein in PBS, at room temperature for 2 hr. Samples of lysates and supernatants from recombinant baculoviruses carrying a PV-VLP expression cassette wherein the PV-3CD protease is under the control of a *poliovirus* IRES were diluted in diluents, 0.2% casein in PBS, dispensed at 100 µl/well, and were incubated at room temperature for 1 hr and then washed with PBST (0.05%).

For detection of VLPs, mouse monoclonal antibodies, anti-VP1 (Clone 5-D8/1; Dako), were prepared in 0.2% casein in PBS diluents at a 1:250 dilution. The diluted detecting monoclonal antibodies were dispensed at 100 µl/well and then incubated at room temperature for 1 hr. Anti-mouse HRP conjugated 2° antibodies were prepared in 0.2% casein in PBS diluents at a 1:1000 dilution. After washing the plate with PBST (0.05%), 100 µl/well of the diluted 2° antibodies were dispensed and the plate incubated at room temperature for 1 hr. The plates were washed with washing buffer, PBST (0.05%). SureBlue™ TMB 1(KPL) component microwell peroxidase substrate was dispensed at 100 µl/well and incubated at room temperature for 10 min for development. 100 µl/well of stop solution, 5 mM NaOH, was added to stop the reaction. The absorbance of each well was read at an OD of 650 nm.

The results of the two sites ELISA shown in FIG. 23 demonstrate that the VP1 and VP3 proteins are in association with each other indicating that VLPs are indeed formed from the PV-VLP expression cassette.

Example 23. Construction of HEV71 VLP Expression Cassettes with HEV71 IRES (P1+HEV71 IRES+3CD)

The schematic structure of a HEV71 VLP cassette with HEV71-IRES is shown in FIG. 24. The expression cassette is similar to the construct shown in Example 1 (pSN01) except that the expression of the 3CD protease is driven by the HEV71 IRES rather than the EMCV IRES. The HEV71 IRES sequence is found in GenBank, Accession Number DQ341362.1; nucleotides 1 to 747. An HEV71 expression cassette containing vector is introduced into the baculovirus expression plasmid pDEST8 (Destination vector) by attL/aaR in vitro recombination using LR CLONASE®, following the instructions in the Invitrogen BAC-TO-BAC® manual (2009). Recombination between the entry vector and pDEST8 produces an expression clone. Expression clones give rise to recombinant bacmid by transforming DH10bac as described in the Invitrogen BAC-TO-BAC® manual. Transfection of the recombinant bacmid into Sf9 cells rescues the recombinant baculovirus carrying expression cassette which harbors P1, HEV71 IRES and 3CD.

Further infection of Sf9 cells can be used to evaluate expression of processed capsid proteins with rescued recombinant baculoviruses in 6 well plates. A polyclonal rabbit antiserum specific for VP1, VP0 and VP3 will identify the assembled VLPs by Western blotting of lysates and supernatants from recombinant baculovirus infected Sf9 cells.

Example 24. Construction of HEV71 VLP Expression Cassettes with PV-IRES (P1+PV-IRES+3CD)

The expression cassette is similar to the expression cassette in Example 24 except that the expression of the 3CD protease is driven by a *poliovirus* IRES (PV-IRES) rather than an HEV71-IRES. The *poliovirus* IRES sequence is found in GenBank, Accession Number V01150.12; nucleotides 1 to 628.

An HEV71 expression cassette containing vector is introduced into the baculovirus expression plasmid pDEST8 (Destination vector) by attL/aaR in vitro recombination using LR CLONASE®, following the instructions in the Invitrogen BAC-TO-BAC® manual (2009). Recombination reaction between entry vector and pDEST8 is set up to produce an expression clone. An expression clone give rises to recombinant bacmid by transforming DH10bac as described in the Invitrogen BAC-TO-BAC® manual. Transfection of the recombinant bacmid into Sf9 cells rescues the recombinant baculovirus carrying expression cassette which harbors P1, PV IRES and 3CD.

Further infection of Sf9 cells can be used to evaluate for expression of processed capsid proteins with rescued recombinant baculoviruses in 6 well plates. A polyclonal rabbit antiserum specific for VP1, VP0 and VP3 will identify the assembled VLPs by Western blotting of lysates and supernatants from recombinant baculovirus infected Sf9 cells.

The invention claimed is:

1. An expression cassette comprising a promoter operably linked to a nucleic acid sequence encoding a human *enterovirus* C P1 polypeptide, wherein the nucleic acid sequence encoding the human *enterovirus* C P1 polypeptide is operably linked to a nucleic acid sequence encoding a human *enterovirus* C Internal Ribosome Entry Site (IRES), wherein the nucleic acid sequence encoding the IRES is operably linked to a nucleic acid sequence encoding a human *enterovirus* C 3CD protease, wherein the human *enterovirus* C 3CD protease is under the translational control of the IRES.

2. A method of making a vaccine comprising the step of culturing an isolated eukaryotic host cell comprising the expression cassette of claim 1 for a period of time sufficient to produce the human *enterovirus* C P1 polypeptide and human *enterovirus* C 3CD protease and form virus like particles.

3. The method according to claim 2, further comprising the step of recovering the virus like particles from the eukaryotic host cell and/or culture supernatant.

* * * * *

SEQUENCE LISTING

```
<160> NUMBER OF SEQ ID NOS: 3

<210> SEQ ID NO 1
<211> LENGTH: 586
<212> TYPE: RNA
<213> ORGANISM: Encephalomyocarditis virus
<220> FEATURE:
```

```
<221> NAME/KEY: misc_feature
<223> OTHER INFORMATION: internal ribosome entry site

<400> SEQUENCE: 1
gccccucucc cucccccccc ccuaacguua cuggccgaag ccgcuuggaa uaaggccggu      60
guguguuugu cuauauguga uuuuccacca uauugccguc uuuuggcaau gugagggccc     120
ggaaaccugg cccugucuuc uugacgagca uuccuagggg ucuuuccccu cucgccaaag    180
gaaugcaagg ucuguugaau gucgugaagg aagcaguucc ucuggaagcu ucuugaagac    240
aaacaacguc uguagcgacc cuuugcaggc agcggaaccc cccaccuggc gacaggugcc    300
ucugcggcca aaagccacgu guauaagaua caccugcaaa ggcggcacaa ccccagugcc    360
acguugugag uuggauaguu guggaaagag ucaaauggcu cuccucaagc guagucaaca    420
aggggcugaa ggaugcccag aagguacccc auuguauggg aaucugaucu ggggccucgg    480
ugcacaugcu uuacaugugu uuagucgagg uuaaaaaagc ucuaggcccc ccgaaccacg    540
gggacguggu uuuccuuuga aaaacacgau gauaagcuug ccacaa                   586

<210> SEQ ID NO 2
<211> LENGTH: 38
<212> TYPE: RNA
<213> ORGANISM: Encephalomyocarditis virus

<400> SEQUENCE: 2
augauaauau gacuucgaaa guuuaugauc cagaacaa                             38

<210> SEQ ID NO 3
<211> LENGTH: 49
<212> TYPE: RNA
<213> ORGANISM: Artificial Sequence
<220> FEATURE:
<223> OTHER INFORMATION: Synthesized mutation

<400> SEQUENCE: 3
augauaagcu ugccacaacc cgggauccuc uagagucgac augacuucg                 49
```